United States Patent
Murakami et al.

(10) Patent No.: US 8,697,889 B2
(45) Date of Patent: Apr. 15, 2014

(54) METAL COMPOUND, POLYMERIZABLE COMPOSITION CONTAINING THE SAME, RESIN, METHOD FOR PRODUCING THE RESIN, AND USE OF THE RESIN

(75) Inventors: Masakazu Murakami, Omuta (JP); Mamoru Takashina, Omuta (JP); Tomoyuki Ando, Omuta (JP); Seiichi Kobayashi, Omuta (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 502 days.

(21) Appl. No.: 12/993,057

(22) PCT Filed: May 15, 2009

(86) PCT No.: PCT/JP2009/002139
§ 371 (c)(1),
(2), (4) Date: Nov. 16, 2010

(87) PCT Pub. No.: WO2009/141984
PCT Pub. Date: Nov. 26, 2009

(65) Prior Publication Data
US 2011/0136977 A1 Jun. 9, 2011

(30) Foreign Application Priority Data
May 19, 2008 (JP) .................................. 2008-130453
Aug. 1, 2008 (JP) .................................. 2008-199521

(51) Int. Cl.
*C07D 331/04* (2006.01)

(52) U.S. Cl.
USPC ................. 549/3; 549/88; 524/857; 528/373; 528/375; 528/380

(58) Field of Classification Search
USPC .......... 549/3, 88; 524/857; 528/373, 375, 380
See application file for complete search history.

(56) References Cited

U.S. PATENT DOCUMENTS

| | | | |
|---|---|---|---|
| 7,723,318 B2 * | 5/2010 | Otsuji et al. ..................... | 514/63 |
| 8,293,864 B2 * | 10/2012 | Murakami et al. ............ | 528/380 |
| 8,349,996 B2 * | 1/2013 | Murakami et al. ............ | 528/375 |
| 8,362,280 B2 * | 1/2013 | Kuboi et al. .................... | 549/88 |
| 8,420,718 B2 * | 4/2013 | Ando et al. ...................... | 524/83 |
| 8,426,551 B2 * | 4/2013 | Murakami et al. ............ | 528/380 |
| 2005/0215757 A1 | 9/2005 | Kobayashi et al. | |
| 2007/0191615 A1* | 8/2007 | Otsuji et al. ..................... | 549/3 |
| 2009/0076208 A1* | 3/2009 | Usugi et al. .................... | 524/420 |
| 2010/0063246 A1* | 3/2010 | Usugi et al. .................... | 528/375 |
| 2010/0240862 A1* | 9/2010 | Murakami et al. ............ | 528/380 |
| 2010/0298519 A1* | 11/2010 | Nakamura et al. ................ | 528/9 |
| 2011/0118412 A1* | 5/2011 | Kuboi et al. .................... | 524/857 |
| 2011/0136977 A1* | 6/2011 | Murakami et al. ............ | 524/857 |

FOREIGN PATENT DOCUMENTS

| | | |
|---|---|---|
| EP | 2 014 700 A1 | 1/2009 |
| JP | 61-166804 A | 7/1986 |
| JP | 2003-327583 A | 11/2003 |
| WO | WO 2005/095490 A1 | 10/2005 |
| WO | WO 2007/099702 A1 | 9/2007 |
| WO | WO 2007/125636 A1 | 11/2007 |
| WO | WO 2007/148439 A1 | 12/2007 |

OTHER PUBLICATIONS

International Search Report (PCT/ISA/210) issued on Aug. 11, 2009, by Japanese Patent Office as the International Searching Authority for International Application No. PCT/JP2009/002139.
Sun Yuanhong et al., "Studies on L-Cysteine Complexes of Lanthanide Chlorides—Its' Preparation, FT-IR and XPS", Yingyong Huaxue, Dec. 1989, vol. 6, No. 6, pp. 32-37, Chinese Journal of Applied Chemistry, China.
Zhu Jiaqin et al., "Studied on the Synthesis and Structure of Several Bi-unit and Tri-unit Complex of α-Aminoacid with Rare Earth", Zhongshan Daxue Xuebao, Oct. 1992, vol. 31, No. 4, pp. 57-62, Acta Scientiarum Naturalium Universitatis Sunyatseni, China.
Ashok Kothari et al.: "A study of ternary complexes of praseodymium with cysteine and diols", Journal of Inorganic and Nuclear Chemistry, vol. 43, No. 11, Jan. 1, 1981, pp. 2905-2908.
Search Report dated Apr. 17, 2013 issued in corresponding EP 09 75 0346.

* cited by examiner

Primary Examiner — Michael Pepitone
Assistant Examiner — Michael A Salvitti
(74) Attorney, Agent, or Firm — Buchanan Ingersoll & Rooney PC

(57) ABSTRACT

Disclosed is a metal compound represented by the following formula (0):
in the formula (0), A represents a thietane ring, or a monovalent group containing a thiol group; B represents a divalent group containing a heteroatom; $R^2$ represents a divalent organic group;
n represents the valence of M; p represents an integer of 1 ton;
M represents a lanthanoid atom or a barium (Ba) atom when A is a thietane ring, and represents a lanthanoid atom when A is a monovalent group containing a thiol group;
or more than Y represents a monovalent inorganic or organic group; when n−p is not less than 2, a plurality of Y's each independently represent a monovalent inorganic or organic group; and when n−p is not less than 2, the plurality of Y's may be bonded with each other to form a ring containing M.

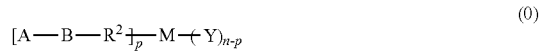

(0)

12 Claims, No Drawings

METAL COMPOUND, POLYMERIZABLE COMPOSITION CONTAINING THE SAME, RESIN, METHOD FOR PRODUCING THE RESIN, AND USE OF THE RESIN

TECHNICAL FIELD

The present invention relates to a metal compound, a polymerizable composition containing the same, a resin, and a method for producing the resin, and use of the resin.

BACKGROUND ART

In recent years, transparent organic polymer materials are used as transparent materials that replace inorganic glass. When these materials are used in optical resins, generally, the materials are required to have characteristics that are generally requested, for example, transparency, thermal properties and mechanical properties, and to have high refractive indices.

One of the technologies relating to such a resin is described in Patent Document 1. In the same document, a metal-containing thietane compound is described. Furthermore, a high-refractive index optical resin having a refractive index (nd) exceeding 1.7 is described. Patent Document 3 describes a method for producing a resin using a lanthanoid-containing thiol.

[Patent Document 1] WO 2005/095490

[Patent Document 2] Japanese Laid-open patent publication No. 2003-327583

[Patent Document 3] Japanese Laid-open patent publication No. 61-166804

DISCLOSURE OF THE INVENTION

However, even those technologies described above have room for further improvement in the aspect of enhancing the balance between the refractive index and the Abbe number.

The present invention is as follows.

[1] A metal compound represented by the following formula (0):

In the formula (0), A represents a monovalent group containing a thietane ring or a thiol group; B represents a divalent group containing a heteroatom; and $R^2$ represents a divalent organic group.

M represents a lanthanoid atom or a barium (Ba) atom when A is a monovalent group containing a thietane ring, and represents a lanthanoid atom when A is a monovalent group containing a thiol group.

n represents the valence of M; and p represents an integer of 1 to n.

Y represents a monovalent inorganic or organic group; when n–p is not less than 2, a plurality of Y's each independently represent a monovalent inorganic or organic group; and when n–p is not less than 2, the plurality of Y's may be bonded with each other to form a ring containing M.

[2] The metal compound as set forth in [1], which is represented by the following formula (1):

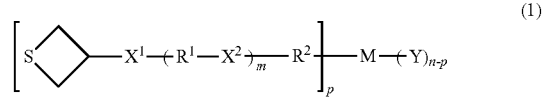

In the formula (1), $X^1$ and $X^2$ each independently represent a sulfur atom or an oxygen atom; $R^1$ and $R^2$ each independently represent a divalent organic group;

m represents an integer of 0 or not less than 1; M represents a lanthanoid atom or a Ba atom; n represents the valence of M; p represents an integer of 1 to n;

Y represents a monovalent inorganic or organic group; when n–p is not less than 2, a plurality of Y's each independently represent a monovalent inorganic or organic group; and when n–p is not less than 2, the plurality of Y's may be bonded with each other to form a ring containing M.

[3] The metal compound as set forth in [2], wherein M represents a lanthanum (La) atom.

[4] The metal compound as set forth in [2], wherein M represents any one of a neodymium (Nd) atom, a gadolinium (Gd) atom and a cerium (Ce) atom.

[5] The metal compound as set forth in [3] or [4], wherein m=0.

[6] The metal compound as set forth in [5], wherein $X^1$ represents a sulfur atom.

[7] The metal compound as set forth in [6], wherein $R^2$ represents a —$CH_2(C=O)O$— group.

[8] The metal compound as set forth in [7], wherein n=p.

[9] The metal compound as set forth in [1], which is represented by formula (101):

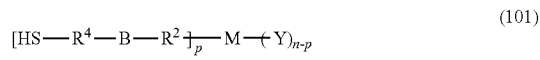

In the formula (101), B represents a divalent group containing a heteroatom; $R^2$ and $R^4$ each independently represent a divalent organic group;

M represents a lanthanoid atom; n represents the valence of M; p represents an integer of 1 to n;

Y represents a monovalent inorganic or organic group; when n–p is not less than 2, a plurality of Y's each independently represent a monovalent organic or inorganic group; and when n–p is not less than 2, the plurality of Y's may be bonded with each other to form a ring containing M.

[10] The metal compound as set forth in [9], which is represented by the following formula (102):

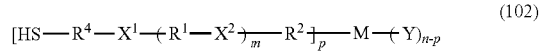

In the formula (102), $X^1$ and $X^2$ each independently represent a sulfur atom or an oxygen atom; $R^1$, $R^2$ and $R^4$ each independently represent a divalent organic group;

m represents an integer of 0 or not less than 1; M represents a lanthanoid atom; n is the valence of M; p is an integer of 1 to n;

Y represents an inorganic or organic group; when n–p is not less than 2, a plurality of Y each independently represent a monovalent inorganic or organic group; and when n–p is not less than 2, the plurality of Y's may be bonded with each other to form a ring containing M.

[11] The metal compound as set forth in [10], wherein $R^4$ represents a substituted or unsubstituted alkylene group.

[12] The metal compound as set forth in [11], wherein m=0.

[13] The metal compound as set forth in [12], wherein $X^1$ represents a sulfur atom.

[14] The metal compound as set forth in [13], wherein $R^2$ represents a —$CH_2(C=O)O$— group.

[15] The metal compound as set forth in [13], wherein n=p.

[16] The metal compound as set forth in any one of [9] to [15], wherein M is an La atom.

[17] A polymerizable composition containing the metal compound as set forth in any one of [1] to [16].

[18] The polymerizable composition as set forth in [17], containing the metal compound and further containing one or more kind selected from the group consisting of an isocyanate compound, an active hydrogen compound, an epoxy compound, an epithio compound and a thietane compound.

[19] The polymerizable composition as set forth in [17] or [18], further containing a bluing agent.

[20] A method for producing a resin, the method including cast polymerizing the polymerizable composition as set forth in any one of [17] or [19].

[21] A resin obtainable by polymerizing the polymerizable composition as set forth in any one of [17] to [19].

[22] An optical component formed from the resin as set forth in [21].

[23] Use of the polymerizable composition as set forth in any one of [17] to [19], as an optical component.

[24] An optical component formed from a resin obtained by polymerizing the polymerizable composition as set forth in any one of [17] to [19].

According to the present invention, there is provided a novel compound which gives a transparent resin that is excellent in a balance between the refractive index and the Abbe number.

BEST MODE FOR CARRYING OUT THE INVENTION

Hereinafter, the invention will be described by using specific examples, but the invention is not intended to be limited to these. Furthermore, in regard to the various components or groups mentioned for the invention, those exemplary components or groups may be used singly, or a plurality may be used in combination. The organic group may contain a heteroatom in the group, in addition to carbon atoms and hydrogen atoms. Specific examples of the heteroatom include an oxygen atom, a sulfur atom and a nitrogen atom.

First, the metal compound of the invention will be explained.

The metal compound of the invention is represented by the following formula (0).

(In the formula (0), A represents a monovalent group containing a thietane ring or a thiol group; B represents a divalent group containing a heteroatom; $R^2$ represents a divalent organic group;

M represents a lanthanoid atom or a Ba atom when A is a monovalent group containing a thietane ring, and represents a lanthanoid atom when A is a monovalent group containing a thiol group;

n is the valence of M; p represents an integer of 1 to n; Y represents a monovalent inorganic or organic group; when n−p is not less than 2, a plurality of Y's each independently represent a monovalent inorganic or organic group; and when n−p is not less than 2, the plurality of Y's may be bonded with each other to form a ring containing M.)

The metal compound represented by this formula (0) is, for example, a compound for optical components.

An example of the metal compound represented by the formula (0) is a compound represented by the following formula (1), which contains a thiethanyl group and a metal atom (lanthanoid atom) in the molecule.

When such a compound is used, a transparent resin that is excellent in the balance between the refractive index and the Abbe number may be obtained.

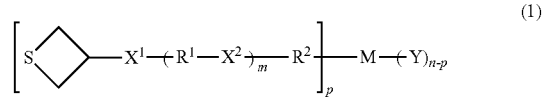

(In the formula (1), $R^2$, Y, n and p have the same definitions as $R^2$, Y, n and p of the formula (0); M represents a lanthanoid atom or a Ba atom; $X^1$ and $X^2$ each independently represent a sulfur atom or an oxygen atom; $R^1$ and $R^2$ each independently represent a divalent organic group; and m represents an integer of 0 or not less than 1).

When such a compound is used, a transparent resin having a high refractive index and a high Abbe number may be certainly obtained.

Another example of the metal compound represented by the formula (0) is a compound represented by the following formula (101), which contains a thiol group and a metal atom (lanthanoid atom) in the molecule.

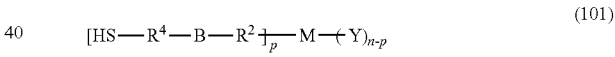

(In the formula (101), B, $R^2$, Y, n and p have the same definitions as B, $R^2$, Y, n and p of the formula (0); M represents a lanthanoid atom; $R^4$ and $R^2$ each independently represent a divalent organic group.)

When such a compound is used, a transparent resin having a high refractive index and capable of suppressing a decrease in the Abbe number may be certainly obtained.

First, the compound represented by the formula (1) will be described.

In the formula (1), $X^1$ and $X^2$ each independently represent a sulfur atom or an oxygen atom. From the viewpoint of increasing the refractive index of the resin obtainable by polymerizing the compound represented by the formula (1), a sulfur atom is more preferable for $X^1$ and $X^2$.

In the formula (1), $R^1$ represents a divalent organic group.

Examples of such a divalent organic group include a chain-like or cyclic aliphatic group, an aromatic group and an aromatic-aliphatic group. Preferable examples include a chain-like aliphatic group having 1 to 20 carbon atoms, a cyclic aliphatic group having 3 to 20 carbon atoms, an aromatic group having 5 to 20 carbon atoms, and an aromatic-aliphatic group having 6 to 20 carbon atoms.

$R^1$ is more specifically such that such a divalent organic group is a chain-like or cyclic aliphatic group, an aromatic group or an aromatic-aliphatic group, and is preferably a substituted or unsubstituted chain-like or cyclic aliphatic group having 1 to 20 carbon atoms, such as a methylene group, an ethylene group, a 1,2-dichloroethylene group, a trimethylene group, a tetramethylene group, a pentamethylene group, a cyclopentylene group, a hexamethylene group, a cyclohexylene group, a heptamethylene group, an octamethylene group, a nonamethylene group, a decamethylene group, an undecamethylene group, a dodecamethylene group, a tridecamethylene group, a tetradecamethylene group, or a pentadecamethylene group;

a substituted or unsubstituted aromatic group having 5 to 20 carbon atoms, such as a phenylene group, a chlorophenylene group, a naphthylene group, an indenylene group, an anthracenylene group, or a fluorenylene group; or a substituted or unsubstituted aromatic-aliphatic group having 6 to 20 carbon atoms, such as a —$C_6H_4$—$CH_2$— group, a —$CH_2$—$C_6H_4$—$CH_2$— group, a —$CH_2$—$C_6H_3$(Cl)—$CH_2$— group, a —$C_{10}H_6$—$CH_2$— group, a —$CH_2$—$C_{10}H_6$—$CH_2$— group, or a —$CH_2CH_2$—$C_6H_4$—$CH_2CH_2$— group.

$R^1$ is more preferably a substituted or unsubstituted chain-like or cyclic aliphatic group having 1 to 6 carbon atoms, such as a methylene group, an ethylene group, a 1,2-dichloroethylene group, a trimethylene group, a cyclopentylene group, or a cyclohexylene group;

a substituted or unsubstituted aromatic group having 5 to 15 carbon atoms, such as a phenylene group, a chlorophenylene group, a naphthylene group, an indenylene group, an anthracenylene group, or a fluorenylene group; or a substituted or unsubstituted aromatic-aliphatic group having 6 to 15 carbon atoms, such as a —$C_6H_4$—$CH_2$— group, a —$CH_2$—$C_6H_4$—$CH_2$— group, a —$CH_2$—$C_6H_3$(Cl)—$CH_2$— group, a —$C_{10}H_6$—$CH_2$— group, a —$CH_2$—$C_{10}H_6$—$CH_2$— group, or a —$CH_2CH_2$—$C_6H_4$—$CH_2CH_2$— group.

Such a divalent organic group may contain a heteroatom in the group, in addition to carbon atoms and hydrogen atoms. Such a heteroatom may be an oxygen atom or a sulfur atom, but upon consideration of the desired effects of the invention, the heteroatom is preferably a sulfur atom.

In the formula (1), M is a lanthanoid atom or a Ba atom. Among others, M is preferably any one of a La atom, a Nd atom, a Gd atom, a Ce atom and a Ba atom, from the viewpoint of increasing the refractive index of the resin obtainable by polymerizing the compound represented by the formula (1).

In the formula (1), n is the valence of M (metal atom).

Furthermore, p is a positive integer of not more than the valence of M. For example, when M is any of a La atom, a Nd atom, a Gd atom and a Ce atom, p is an integer of 1 to 3. When M is a Ba atom, p is an integer of 1 to 2.

Furthermore, m is an integer of 0 or not less than 1. m is preferably an integer of 0 to 4, more preferably an integer of 0 to 2, and even more preferably 0 or 1.

When m=0, the formula (1) turns into the following formula (2).

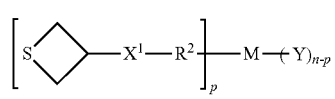

(In the formula (2), $X^1$, $R^2$, Y, M, n and p respectively have the same definitions as $X^1$, $R^2$, Y, M, n and p of the formula (1).)

In regard to the group that contains a thiethanyl group and is bound to M in the formula (1), that is, the monovalent group shown within the brackets [ ], more preferably m=0, and $X^1$ is a sulfur atom. In this case, the formula (1) is represented by the following formula (3).

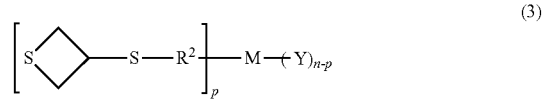

(In the formula (3), $R^2$, Y, M, n and p respectively have the same definitions as $R^2$, Y, M, n and p of the formula (1).)

In the formula (3), more preferably n=p, and in this case, the formula (3) turns into the following formula (4).

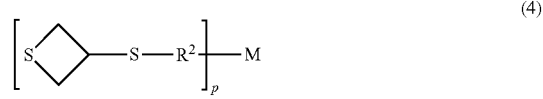

(In the formula (4), $R^2$, M and p have the same definitions as $R^2$, M and p of the formula (1).)

Returning to the formula (1), $R^2$ is a divalent organic group. $R^2$ may be specifically a group represented by —(C=P)O— or —$R^3$(C=O)O— (wherein $R^3$ represents an alkylene group having 1 to 4 carbon atoms). From the viewpoint of the stability of the compound represented by the formula (1) or an increase in the refractive index, it is preferable that $R^3$ is a methylene group, that is, $R^2$ is a —$CH_2$ (C=O)O— group. Furthermore, when $R^2$ is a —$CH_2$ (C=O)O— group, for example, m may be 0, and $X^1$ may be a sulfur atom. When $R^2$ is —$CH_2$ (C=O)O— group, it may be such that m=0, $X^1$ is a sulfur atom, and n=p. In this case, the formula (1) turns into a compound represented by the following formula (5).

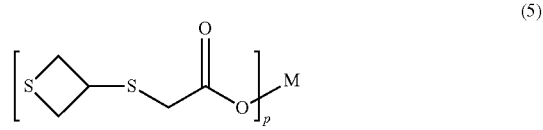

(In the formula (5), M and p have the same definitions as M and p of the formula (1).)

Returning to the formula (1), Y is a monovalent inorganic or organic group, and more specifically a monovalent organic group. When n–p is not less than 2, a plurality of Y's each independently represent a monovalent group. That is, the plurality of Y's may be identical groups, or all or a part may be different groups. Also, when n–p is not less than 2, the plurality of Y's may be bonded with each other to form a ring containing M. Specific examples of Y will be described below.

Y is not particularly limited, but examples include a hydrogen atom, a halogen atom, a hydroxyl group, a thiol group, a substituted or unsubstituted alkyl group, a substituted or unsubstituted aryl group, a substituted or unsubstituted aralkyl group, a substituted or unsubstituted alkoxy group, a substituted or unsubstituted alkylthio group, a substituted or unsubstituted aryloxy group, a substituted or unsubstituted arylthio group, a substituted or unsubstituted carboxylic acid group, and a substituted or unsubstituted sulfonic acid group.

Among these, an explanation will be given concerning a halogen atom, a substituted or unsubstituted alkyl group, a substituted or unsubstituted aryl group, a substituted or unsubstituted aralkyl group, a substituted or unsubstituted alkoxy (alkyloxy) group, a substituted or unsubstituted alkylthio group, a substituted or unsubstituted aryloxy group, a substituted or unsubstituted arylthio group, a substituted or unsubstituted carboxylic acid group, and a substituted or unsubstituted sulfonic acid group.

Specific examples of the halogen atom include a fluorine atom, a chlorine atom, a bromine atom and an iodine atom.

Specific examples of the substituted or unsubstituted alkyl group include a linear alkyl group having 1 to 10 carbon atoms in total, such as a methyl group, an ethyl group, an n-propyl group, an n-butyl group, an n-pentyl group, or an n-hexyl group;

a branched alkyl group having 3 to 10 carbon atoms in total, such as an isopropyl group, an isobutyl group, a sec-butyl group, an isopentyl group, a sec-pentyl group, a 1-methylpentyl group, a 2-methylpentyl group, a 3-methylpentyl group, a 4-methylpentyl group, a 1-ethylbutyl group, a 2-ethylbutyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 1-n-propylbutyl group, a 1-iso-propylbutyl group, a 1-iso-propyl-2-methylpropyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 1-n-propylpentyl group, a 2-n-propylpentyl group, a 1-iso-propylpentyl group, a 2-iso-propylpentyl group, a 1-n-butylbutyl group, a 1-iso-butylbutyl group, a 1-sec-butylbutyl group, a 1-tert-butylbutyl group, a 2-tert-butylbutyl group, a tert-butyl group, a tert-pentyl group, a 1,1-dimethylbutyl group, a 1,2-dimethylbutyl group, a 1,3-dimethylbutyl group, a 2,3-dimethylbutyl group, a 1-ethyl-2-methylpropyl group, a 1,1-dimethylpentyl group, a 1,2-dimethylpentyl group, a 1,3-dimethylpentyl group, a 1,4-dimethylpentyl group, a 2,2-dimethylpentyl group, a 2,3-dimethylpentyl group, a 2,4-dimethylpentyl group, a 3,3-dimethylpentyl group, a 3,4-dimethylpentyl group, a 1-ethyl-1-methylbutyl group, a 1-ethyl-2-methylbutyl group, a 1-ethyl-3-methylbutyl group, a 2-ethyl-1-methylbutyl group, a 2-ethyl-3-methylbutyl group, a 1,1-dimethylhexyl group, a 1,2-dimethylhexyl group, a 1,3-dimethylhexyl group, a 1,4-dimethylhexyl group, a 1,5-dimethylhexyl group, a 2,2-dimethylhexyl group, a 2,3-dimethylhexyl group, a 2,4-dimethylhexyl group, a 2,5-dimethylhexyl group, a 3,3-dimethylhexyl group, a 3,4-dimethylhexyl group, a 3,5-dimethylhexyl group, a 4,4-dimethylhexyl group, a 4,5-dimethylhexyl group, a 1-ethyl-2-methylpentyl group, a 1-ethyl-3-methylpentyl group, a 1-ethyl-4-methylpentyl group, a 2-ethyl-1-methylpentyl group, a 2-ethyl-2-methylpentyl group, a 2-ethyl-3-methylpentyl group, a 2-ethyl-4-methylpentyl group, a 3-ethyl-1-methylpentyl group, a 3-ethyl-2-methylpentyl group, a 3-ethyl-3-methylpentyl group, a 3-ethyl-4-methylpentyl group, a 1-n-propyl-1-methylbutyl group, a 1-n-propyl-2-methylbutyl group, a 1-n-propyl-3-methylbutyl group, a 1-iso-propyl-1-methylbutyl group, a 1-iso-propyl-2-methylbutyl group, a 1-iso-propyl-3-methylbutyl group, a 1,1-diethylbutyl group, a 1,2-diethylbutyl group, a 1,1,2-trimethylpropyl group, a 1,2,2-trimethylpropyl group, a 1,1,2-trimethylbutyl group, a 1,1,3-trimethylbutyl group, a 1,2,3-trimethylbutyl group, a 1,2,2-trimethylbutyl group, a 1,3,3-trimethylbutyl group, a 2,3,3-trimethylbutyl group, a 1,1,2-trimethylpentyl group, a 1,1,3-trimethylpentyl group, a 1,1,4-trimethylpentyl group, a 1,2,2-trimethylpentyl group, a 1,2,3-trimethylpentyl group, a 1,2,4-trimethylpentyl group, a 1,3,4-trimethylpentyl group, a 2,2,3-trimethylpentyl group, a 2,3,4-trimethylpentyl group, a 1,3,3-trimethylpentyl group, a 2,3,3-trimethylpentyl group, a 3,3,4-trimethylpentyl group, a 1,4,4-trimethylpentyl group, a 2,4,4-trimethylpentyl group, a 3,4,4-trimethylpentyl group, a 1-ethyl-1,2-dimethylbutyl group, a 1-ethyl-1,3-dimethylbutyl group, a 1-ethyl-2,3-dimethylbutyl group, a 2-ethyl-1,1-dimethylbutyl group, a 2-ethyl-1,2-dimethylbutyl group, a 2-ethyl-1,3-dimethylbutyl group, or a 2-ethyl-2,3-dimethylbutyl group; and a saturated cyclic alkyl group having 5 to 10 carbon atoms in total, such as a cyclopentyl group, a cyclohexyl group, a methylcyclopentyl group, a methoxycyclopentyl group, a methoxycyclohexyl group, a methylcyclohexyl group, a 1,2-dimethylcyclohexyl group, a 1,3-dimethylcyclohexyl group, a 1,4-dimethylcyclohexyl group, or an ethylcyclohexyl group.

Specific examples of the substituted or unsubstituted aryl group include an aromatic hydrocarbon having not more than 20 carbon atoms in total, such as a phenyl group, a naphthyl group, an anthranyl group, or a cyclopentadienyl group;

an alkyl-substituted aryl group having not more than 20 carbon atoms in total, such as a 2-methylphenyl group, a 3-methylphenyl group, a 4-methylphenyl group, a 2-ethylphenyl group, a propylphenyl group, a butylphenyl group, a hexylphenyl group, a cyclohexylphenyl group, an octylphenyl group, a 2-methyl-1-naphthyl group, a 3-methyl-1-naphthyl group, a 4-methyl-1-naphthyl group, a 5-methyl-1-naphthyl group, a 6-methyl-1-naphthyl group, a 7-methyl-1-naphthyl group, an 8-methyl-1-naphthyl group, a 1-methyl-2-naphthyl group, a 3-methyl-2-naphthyl group, a 4-methyl-2-naphthyl group, a 5-methyl-2-naphthyl group, a 6-methyl-2-naphthyl group, a 7-methyl-2-naphthyl group, an 8-methyl-2-naphthyl group, a 2-ethyl-1-naphthyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 3,6-dimethylphenyl group, a 2,3,4-trimethylphenyl group, a 2,3,5-trimethylphenyl group, a 2,3,6-trimethylphenyl group, a 2,4,5-trimethylphenyl group, a 2,4,6-trimethylphenyl group, or a 3,4,5-trimethylphenyl group;

a monoalkoxyaryl group having less than or equal to 20 carbon atoms in total, which is substituted with a substituted or unsubstituted alkyloxy group having not more than 10 carbon atoms, such as a 2-methoxyphenyl group, a 3-methoxyphenyl group, a 4-methoxyphenyl group, a 2-ethoxyphenyl group, a propoxyphenyl group, a butoxyphenyl group, a hexyloxyphenyl group, a cyclohexyloxyphenyl group, an octyloxyphenyl group, a 2-methoxy-1-naphthyl group, a 3-methoxy-1-naphthyl group, a 4-methoxy-1-naphthyl group, a 5-methoxy-1-naphthyl group, a 6-methoxy-1-naphthyl group, a 7-methoxy-1-naphthyl group, an 8-methoxy-1-naphthyl group, a 1-methoxy-2-naphthyl group, a 3-methoxy-2-naphthyl group, a 4-methoxy-2-naphthyl group, a 5-methoxy-2-naphthyl group, a 6-methoxy-2-naphthyl group, a 7-methoxy-2-naphthyl group, an 8-methoxy-2-naphthyl group, or a 2-ethoxy-1-naphthyl group;

a dialkoxyaryl group having not more than 20 carbon atoms in total, which is substituted with a substituted or unsubstituted alkyloxy group having not more than 10 carbon atoms, such as a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 3,6-dimethoxyphenyl group, a 4,5-dimethoxy-1-naphthyl group, a 4,7-dimethoxy-1-naphthyl group, a 4,8-dimethoxy-1-naphthyl group, a 5,8-dimethoxy-1-naphthyl group, or a 5,8-dimethoxy-2-naphthyl group;

a trialkoxyaryl group having not more than 20 carbon atoms in total, which is substituted with a substituted or unsubstituted alkyloxy group having not more than 10 carbon atoms, such as a 2,3,4-trimethoxyphenyl group, a 2,3,5-trimethoxyphenyl group, a 2,3,6-trimethoxyphenyl group, a 2,4,5-trimethoxyphenyl group, a 2,4,6-trimethoxyphenyl group, or a 3,4,5-trimethoxyphenyl group; and an aryl group having not more than 20 carbon atoms in total, which is substituted with a halogen atom, such as a chlorophenyl group, a dichlorophenyl group, a trichlorophenyl group, a bromophenyl group, a dibromophenyl group, an iodophenyl group, a fluorophenyl group, a chloronaphthyl group, a bromonaphthyl group, a difluorophenyl group, a trifluorophenyl group, a tetrafluorophenyl group, or a pentafluorophenyl group.

A specific example of the substituted or unsubstituted aralkyl group may be an aralkyl group having not more than 12 carbon atoms in total, such as a benzyl group, a phenethyl group, a phenylpropyl group, or a naphthylethyl group. Other examples include a methyl group, an ethyl group and a propyl group, which have, in their side chains, the aryl groups mentioned as specific examples of the substituted or unsubstituted aryl group.

Specific examples of the substituted or unsubstituted alkyloxy group include a linear or branched alkoxy group having 1 to 10 carbon atoms in total, such as a methoxy group, an ethoxy group, an n-propoxy group, an iso-propoxy group, an n-butoxy group, an iso-butoxy group, a tert-butoxy group, an n-pentyloxy group, an iso-pentyloxy group, an n-hexyloxy group, an iso-hexyloxy group, a 2-ethylhexyloxy group, a 3,5,5-trimethylhexyloxy group, an n-heptyloxy group, an n-octyloxy group, or an n-nonyloxy group;

a cycloalkoxy group having 5 to 10 carbon atoms in total, such as a cyclopentyloxy group, or a cyclohexyloxy group;

an alkoxyalkoxy group having 2 to 10 carbon atoms in total, such as a methoxymethoxy group, an ethoxymethoxy group, an ethoxyethoxy group, an n-propoxymethoxy group, an iso-propoxymethoxy group, an n-propoxyethoxy group, an iso-propoxyethoxy group, an n-butoxyethoxy group, an iso-butoxyethoxy group, a tert-butoxyethoxy group, an n-pentyloxyethoxy group, an iso-pentyloxyethoxy group, an n-hexyloxyethoxy group, an iso-hexyloxyethoxy group, or an n-heptyloxyethoxy group; and an aralkyloxy group such as a benzyloxy group.

Specific examples of the substituted or unsubstituted alkylthio group include a linear or branched alkylthio group having 1 to 10 carbon atoms in total, such as a methylthio group, an ethylthio group, an n-propylthio group, an iso-propylthio group, an n-butylthio group, an iso-butylthio group, a sec-butylthio group, a t-butylthio group, an n-pentylthio group, an iso-pentylthio group, an n-hexylthio group, an iso-hexylthio group, a 2-ethylhexylthio group, a 3,5,5-trimethylhexylthio group, an n-heptylthio group, an n-octylthio group, or an n-nonylthio group;

a cycloalkylthio group having 5 to 10 carbon atoms in total, such as a cyclopentylthio group, or a cyclohexylthio group;

an alkoxyalkylthio group having 2 to 10 carbon atoms in total, such as a methoxyethylthio group, an ethoxyethylthio group, an n-propoxyethylthio group, an iso-propoxyethylthio group, an n-butoxyethylthio group, an iso-butoxyethylthio group, a tert-butoxyethylthio group, an n-pentyloxyethylthio group, an iso-pentyloxyethylthio group, an n-hexyloxyethylthio group, an iso-hexyloxyethylthio group, or an n-heptyloxyethylthio group;

an aralkylthio group such as a benzylthio group; and an alkylthioalkylthio group having 2 to 10 carbon atoms in total, such as a methylthioethylthio group, an ethylthioethylthio group, an n-propylthioethylthio group, an iso-propylthioethylthio group, an n-butylthioethylthio group, an iso-butylthioethylthio group, a tert-butylthioethylthio group, an n-pentylthioethylthio group, an iso-pentylthioethylthio group, an n-hexylthioethylthio group, an iso-hexylthioethylthio group, or an n-heptylthioethylthio group.

Specific examples of the substituted or unsubstituted aryloxy group include an unsubstituted or alkyl-substituted aryloxy group having not more than 20 carbon atoms in total, such as a phenyloxy group, a naphthyloxy group, an anthranyloxy group, a 2-methylphenyloxy group, a 3-methylphenyloxy group, a 4-methylphenyloxy group, a 2-ethylphenyloxy group, a propylphenyloxy group, a butylphenyloxy group, a hexylphenyloxy group, a cyclohexylphenyloxy group, an octylphenyloxy group, a 2-methyl-1-naphthyloxy group, a 3-methyl-1-naphthyloxy group, a 4-methyl-1-naphthyloxy group, a 5-methyl-1-naphthyloxy group, a 6-methyl-1-naphthyloxy group, a 7-methyl-1-naphthyloxy group, an 8-methyl-1-naphthyloxy group, a 1-methyl-2-naphthyloxy group, a 3-methyl-2-naphthyloxy group, a 4-methyl-2-naphthyloxy group, a 5-methyl-2-naphthyloxy group, a 6-methyl-2-naphthyloxy group, a 7-methyl-2-naphthyloxy group, an 8-methyl-2-naphthyloxy group, a 2-ethyl-1-naphthyloxy group, a 2,3-dimethylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, a 3,6-dimethylphenyloxy group, a 2,3,4-trimethylphenyloxy group, a 2,3,5-trimethylphenyloxy group, a 2,3,6-trimethylphenyloxy group, a 2,4,5-trimethylphenyloxy group, a 2,4,6-trimethylphenyloxy group, or a 3,4,5-trimethylphenyloxy group;

a monoalkoxyaryloxy group having not more than 20 carbon atoms in total, which is substituted with a substituted or unsubstituted alkyloxy group having not more than 10 carbon atoms, such as a 2-methoxyphenyloxy group, a 3-methoxyphenyloxy group, a 4-methoxyphenyloxy group, a 2-ethoxyphenyloxy group, a propoxyphenyloxy group, a butoxyphenyloxy group, a hexyloxyphenyloxy group, a cyclohexyloxyphenyloxy group, an octyloxyphenyloxy group, a 2-methoxy-1-naphthyloxy group, a 3-methoxy-1-naphthyloxy group, a 4-methoxy-1-naphthyloxy group, a 5-methoxy-1-naphthyloxy group, a 6-methoxy-1-naphthyloxy group, a 7-methoxy-1-naphthyloxy group, an 8-methoxy-1-naphthyloxy group, a 1-methoxy-2-naphthyloxy group, a 3-methoxy-2-naphthyloxy group, a 4-methoxy-2-naphthyloxy group, a 5-methoxy-2-naphthyloxy group, a 6-methoxy-2-naphthyloxy group, a 7-methoxy-2-naphthyloxy group, an 8-methoxy-2-naphthyloxy group, or a 2-ethoxy-1-naphthyloxy group;

a dialkoxyaryloxy group having not more than 20 carbon atoms in total, which is substituted with a substituted or unsubstituted alkyloxy group having not more than 10 carbon atoms, such as a 2,3-dimethoxyphenyloxy group, a 2,4-dimethoxyphenyloxy group, a 2,5-dimethoxyphenyloxy group, a 2,6-dimethoxyphenyloxy group, a 3,4-dimethoxyphenyloxy group, a 3,5-dimethoxyphenyloxy group, a 3,6-dimethoxyphenyloxy group, a 4,5-dimethoxy-1-naphthyloxy group, a 4,7-dimethoxy-1-naphthyloxy group, a 4,8-dimethoxy-1-naphthyloxy group, a 5,8-dimethoxy-1-naphthyloxy group, or a 5,8-dimethoxy-2-naphthyloxy group;

a trialkoxyaryloxy group having not more than 20 carbon atoms in total, which is substituted with a substituted or unsubstituted alkyloxy group having not more than 10 carbon atoms, such as a 2,3,4-trimethoxyphenyloxy group, a 2,3,5- trimethoxyphenyloxy group, a 2,3,6-trimethoxyphenyloxy group, a 2,4,5-trimethoxyphenyloxy group, a 2,4,6-trimethoxyphenyloxy group, or a 3,4,5-trimethoxyphenyloxy group; and an aryloxy group having not more than 20 carbon atoms in total, which is substituted with a halogen atom, such as a chlorophenyloxy group, a dichlorophenyloxy group, a trichlorophenyloxy group, a bromophenyloxy group, a dibromophenyloxy group, an iodophenyloxy group, a fluorophenyloxy group, a chloronaphthyloxy group, a bromonaphthyloxy group, a difluorophenyloxy group, a trifluorophenyloxy group, a tetrafluorophenyloxy group, or a pentafluorophenyloxy group.

Specific examples of the substituted or unsubstituted arylthio group include an unsubstituted or alkyl-substituted arylthio group having not more than 20 carbon atoms in total, such as a phenylthio group, a naphthylthio group, an anthranylthio group, a 2-methylphenylthio group, a 3-methylphenylthio group, a 4-methylphenylthio group, a 2-ethylphenylthio group, a propylphenylthio group, a butylphenylthio group, a hexylphenylthio group, a cyclohexylphenylthio group, an octylphenylthio group, a 2-methyl-1-naphthylthio group, a 3-methyl-1-naphthylthio group, a 4-methyl-1-naphthylthio group, a 5-methyl-1-naphthylthio group, a 6-methyl-1-naphthylthio group, a 7-methyl-1-naphthylthio group, an 8-methyl-1-naphthylthio group, a 1-methyl-2-naphthylthio group, a 3-methyl-2-naphthylthio group, a 4-methyl-2-naphthylthio group, a 5-methyl-2-naphthylthio group, a 6-methyl-2-naphthylthio group, a 7-methyl-2-naphthylthio group, an 8-methyl-2-naphthylthio group, a 2-ethyl-1-naphthylthio group, a 2,3-dimethylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 3,6-dimethylphenylthio group, a 2,3,4-trimethylphenylthio group, a 2,3,5-trimethylphenylthio group, a 2,3,6-trimethylphenylthio group, a 2,4,5-trimethylphenylthio group, a 2,4,6-trimethylphenylthio group, or a 3,4,5-trimethylphenylthio group;

a monoalkoxyarylthio group having not more than 20 carbon atoms in total, which is substituted with a substituted or unsubstituted alkyloxy group having not more than 10 carbon atoms, such as a 2-methoxyphenylthio group, a 3-methoxyphenylthio group, a 4-methoxyphenylthio group, a 2-ethoxyphenylthio group, a propoxyphenylthio group, a butoxyphenylthio group, a hexyloxyphenylthio group, a cyclohexyloxyphenylthio group, an octyloxyphenylthio group, a 2-methoxy-1-naphthylthio group, a 3-methoxy-1-naphthylthio group, a 4-methoxy-1-naphthylthio group, a 5-methoxy-1-naphthylthio group, a 6-methoxy-1-naphthylthio group, a 7-methoxy-1-naphthylthio group, an 8-methoxy-1-naphthylthio group, a 1-methoxy-2-naphthylthio group, a 3-methoxy-2-naphthylthio group, a 4-methoxy-2-naphthylthio group, a 5-methoxy-2-naphthylthio group, a 6-methoxy-2-naphthylthio group, a 7-methoxy-2-naphthylthio group, an 8-methoxy-2-naphthylthio group, or a 2-ethoxy-1-naphthylthio group;

a dialkoxyarylthio group having not more than 20 carbon atoms in total, which is substituted with a substituted or unsubstituted alkyloxy group having not more than 10 carbon atoms, such as a 2,3-dimethoxyphenylthio group, a 2,4-dimethoxyphenylthio group, a 2,5-dimethoxyphenylthio group, a 2,6-dimethoxyphenylthio group, a 3,4-dimethoxyphenylthio group, a 3,5-dimethoxyphenylthio group, a 3,6-dimethoxyphenylthio group, a 4,5-dimethoxy-1-naphthylthio group, a 4,7-dimethoxy-1-naphthylthio group, a 4,8-dimethoxy-1-naphthylthio group, a 5,8-dimethoxy-1-naphthylthio group, or a 5,8-dimethoxy-2-naphthylthio group;

a trialkoxyarylthio group having not more than 20 carbon atoms in total, which is substituted with a substituted or unsubstituted alkyloxy group having not more than 10 carbon atoms, such as a 2,3,4-trimethoxyphenylthio group, a 2,3,5-trimethoxyphenylthio group, a 2,3,6-trimethoxyphenylthio group, a 2,4,5-trimethoxyphenylthio group, a 2,4,6-trimethoxyphenylthio group, or a 3,4,5-trimethoxyphenylthio group; and an arylthio group having not more than 20 carbon atoms in total, which is substituted with a halogen atom, such as a chlorophenylthio group, a dichlorophenylthio group, a trichlorophenylthio group, a bromophenylthio group, a dibromophenylthio group, an iodophenylthio group, a fluorophenylthio group, a chloronaphthylthio group, a bromonaphthylthio group, a difluorophenylthio group, a trifluorophenylthio group, a tetrafluorophenylthio group, or a pentafluorophenylthio group.

Specific examples of the substituted or unsubstituted carboxylic acid group include a linear or branched carboxylic acid group having 1 to 10 carbon atoms in total, such as a formic acid group, an acetic acid group, a trifluoroacetic acid group, a propionic acid group, an n-butyric acid group, an iso-butyric acid group, an n-pentanoic acid group, a 2-methylbutanoic acid group, a pivalic acid group, an n-hexanoic acid group, an n-hexanoic acid group, an n-heptanoic acid group, an n-octanoic acid group, an n-nonanoic acid group, or an n-decanoic acid group;

a cycloalkanoic acid group having 5 to 10 carbon atoms in total, such as a cyclopentanoic acid group or a cyclohexanoic acid group; and an aryl acid group such as a benzoic acid group.

Specific examples of the substituted or unsubstituted sulfonic acid group include a linear or branched sulfonic acid group having 1 to 10 carbon atoms in total, such as a methanesulfonic acid group, an ethanesulfonic acid group, a trifluoromethanesulfonic acid group or a toluenesulfonic acid group. Y is not intended to be limited to these.

Preferable examples for such Y will be presented below.

A preferable example may be, for example, a hydrogen atom.

Among the preferable examples of Y, the halogen atom may be a chlorine atom, a bromine atom or an iodine atom.

Examples of the substituted or unsubstituted alkyl group include a linear alkyl group having 1 to 6 carbon atoms in total, such as a methyl group, an ethyl group, an n-propyl group, an n-butyl group, an n-pentyl group, or an n-hexyl group;

a branched alkyl group having 3 to 6 carbon atoms in total, such as an isopropyl group, an isobutyl group, a sec-butyl group, an isopentyl group, a sec-pentyl group, a 1-methylpentyl group, a 2-methylpentyl group, a 3-methylpentyl group, a 4-methylpentyl group, a 1-ethylbutyl group, a 2-ethylbutyl group, a tert-butyl group, a tert-pentyl group, a 1,1-dimethylbutyl group, a 1,2-dimethylbutyl group, a 1,3-dimethylbutyl group, or a 2,3-dimethylbutyl group; and a saturated cyclic alkyl group having 5 or 6 carbon atoms in total, such as a cyclopentyl group, or a cyclohexyl group.

Examples of the substituted or unsubstituted aryl group include an aromatic hydrocarbon having not more than 12 carbon atoms in total, such as a phenyl group, a naphthyl group, or a cyclopentadienyl group;

an alkyl-substituted aryl group having not more than 12 carbon atoms in total, such as a 2-methylphenyl group, a 3-methylphenyl group, a 4-methylphenyl group, a 2-ethylphenyl group, a propylphenyl group, a butylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 3,6-dimethylphenyl group, a 2,3,4-trimethylphenyl group, a 2,3,5-trimethylphenyl group, a 2,3,6-trimethylphenyl group, a 2,4,5-trimethylphenyl group, a 2,4,6-trimethylphenyl group, or a 3,4,5-trimethylphenyl group;

a monoalkoxyaryl group having not more than 12 carbon atoms in total, which is substituted with a substituted or unsubstituted alkyloxy group having not more than 6 carbon atoms, such as a 2-methoxyphenyl group, a 3-methoxyphenyl group, a 4-methoxyphenyl group, a 2-ethoxyphenyl group, a propoxyphenyl group, or a butoxyphenyl group;

a dialkoxyaryl group having not more than 12 carbon atoms in total, which is substituted with a substituted or unsubstituted alkyloxy group having not more than 6 carbon atoms, such as a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, or a 3,6-dimethoxyphenyl group; and an aryl group having not more than 12 carbon atoms in total, which is substituted with a halogen atom, such as a chlorophenyl group, a dichlorophenyl group, a trichlorophenyl group, a bromophenyl group, a dibromophenyl group, an iodophenyl group, a fluorophenyl group, a chloronaphthyl group, a bromonaphthyl group, a difluorophenyl group, a trifluorophenyl group, a tetrafluorophenyl group, or a pentafluorophenyl group.

Examples of the substituted or unsubstituted aralkyl group include an aralkyl group having not more than 12 carbon atoms in total, such as a benzyl group, a phenethyl group, or a phenylpropyl group.

Examples of the substituted or unsubstituted alkyloxy group include a linear or branched alkoxy group having 1 to 6 carbon atoms in total, such as a methoxy group, an ethoxy group, an n-propoxy group, an iso-propoxy group, an n-butoxy group, an iso-butoxy group, a tert-butoxy group, an n-pentyloxy group, an iso-pentyloxy group, an n-hexyloxy group, or an iso-hexyloxy group;

a cycloalkoxy group having 5 or 6 carbon atoms in total, such as a cyclopentyloxy group, or a cyclohexyloxy group; and an alkoxyalkoxy group having not less than 2 and equal to or less 6 carbon atoms in total, such as a methoxymethoxy group, an ethoxymethoxy group, an ethoxyethoxy group, an n-propoxymethoxy group, an iso-propoxymethoxy group, an n-propoxyethoxy group, an iso-propoxyethoxy group, an n-butoxyethoxy group, an iso-butoxyethoxy group, or a tert-butoxyethoxy group.

Examples of the substituted or unsubstituted alkylthio group include a linear or branched alkylthio group having 1 to 6 carbon atoms in total, such as a methylthio group, an ethylthio group, an n-propylthio group, an iso-propylthio group, an n-butylthio group, an iso-butylthio group, a sec-butylthio group, a t-butylthio group, an n-pentylthio group, an iso-pentylthio group, an n-hexylthio group, or an iso-hexylthio group;

a cycloalkylthio group having 5 or 6 carbon atoms in total, such as a cyclopentylthio group, or a cyclohexylthio group; and an alkoxyalkylthio group having 2 to 6 carbon atoms in total, such as a methoxyethylthio group, an ethoxyethylthio group, an n-propoxyethylthio group, an iso-propoxyethylthio group, an n-butoxyethylthio group, an iso-butoxyethylthio group, or a tert-butoxyethylthio group; and an alkylthioalkylthio group having 2 to 6 carbon atoms in total, such as a methylthioethylthio group, an ethylthioethylthio group, an n-propylthioethylthio group, an iso-propylthioethylthio group, an n-butylthioethylthio group, an iso-butylthioethylthio group, or a tert-butylthioethylthio group.

Examples of the substituted or unsubstituted aryloxy group include an unsubstituted or alkyl-substituted aryloxy group having not more than 12 carbon atoms in total, such as a phenyloxy group, a naphthyloxy group, a 2-methylphenyloxy group, a 3-methylphenyloxy group, a 4-methylphenyloxy group, a 2-ethylphenyloxy group, a propylphenyloxy group, a butylphenyloxy group, a hexylphenyloxy group, a cyclohexylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, a 3,6-dimethylphenyloxy group, a 2,3,4-trimethylphenyloxy group, a 2,3,5-trimethylphenyloxy group, a 2,3,6-trimethylphenyloxy group, a 2,4,5-trimethylphenyloxy group, a 2,4,6-trimethylphenyloxy group, or a 3,4,5-trimethylphenyloxy group;

a monoalkoxyaryloxy group having not more than 12 carbon atoms in total, which is substituted with a substituted or unsubstituted alkyloxy group having not more than 6 carbon atoms, such as a 2-methoxyphenyloxy group, a 3-methoxyphenyloxy group, a 4-methoxyphenyloxy group, a 2-ethoxyphenyloxy group, a propoxyphenyloxy group, a butoxyphenyloxy group, a hexyloxyphenyloxy group, or a cyclohexyloxyphenyloxy group;

a dialkoxyaryloxy group having not more than 12 carbon atoms in total, which is substituted with a substituted or unsubstituted alkyloxy group having not more than 6 carbon atoms, such as a 2,3-dimethoxyphenyloxy group, a 2,4-dimethoxyphenyloxy group, a 2,5-dimethoxyphenyloxy group, a 2,6-dimethoxyphenyloxy group, a 3,4-dimethoxyphenyloxy group, a 3,5-dimethoxyphenyloxy group, or a 3,6-dimethoxyphenyloxy group; and an aryloxy group having not more than 12 carbon atoms in total, which is substituted with a halogen atom, such as a chlorophenyloxy group, a dichlorophenyloxy group, a trichlorophenyloxy group, a bromophenyloxy group, a dibromophenyloxy group, an iodophenyloxy group, a fluorophenyloxy group, a chloronaphthyloxy group, a bromonaphthyloxy group, a difluorophenyloxy group, a trifluorophenyloxy group, a tetrafluorophenyloxy group, or a pentafluorophenyloxy group.

Examples of the substituted or unsubstituted arylthio group include an unsubstituted or alkyl-substituted arylthio group having not more than 12 carbon atoms in total, such as a phenylthio group, a naphthylthio group, a 2-methylphenylthio group, a 3-methylphenylthio group, a 4-methylphenylthio group, a 2-ethylphenylthio group, a propylphenylthio group, a butylphenylthio group, a hexylphenylthio group, a cyclohexylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 3,6-dimethylphenylthio group, a 2,3,4-trimethylphenylthio group, a 2,3,5-trimethylphenylthio group, a 2,3,6-trimethylphenylthio group, a 2,4,5-trimethylphenylthio group, a 2,4,6-trimethylphenylthio group, or a 3,4,5-trimethylphenylthio group;

a monoalkoxyarylthio group having not more than 12 carbon atoms in total, which is substituted with a substituted or unsubstituted alkyloxy group having not more than 6 carbon atoms, such as a 2-methoxyphenylthio group, a 3-methoxyphenylthio group, a 4-methoxyphenylthio group, a 2-ethoxyphenylthio group, a propoxyphenylthio group, a butoxyphenylthio group, a hexyloxyphenylthio group, or a cyclohexyloxyphenylthio group;

a dialkoxyarylthio group having not more than 12 carbon atoms in total, which is substituted with a substituted or unsubstituted alkyloxy group having not more than 6 carbon atoms, such as a 2,3-dimethoxyphenylthio group, a 2,4-dimethoxyphenylthio group, a 2,5-dimethoxyphenylthio group, a 2,6-dimethoxyphenylthio group, a 3,4-dimethoxyphenylthio group, a 3,5-dimethoxyphenylthio group, a 3,6-dimethoxyphenylthio group, a 4,5-dimethoxy-1-naphthylthio group, a 4,7-dimethoxy-1-naphthylthio group, a 4,8-dimethoxy-1-naphthylthio group, a 5,8-dimethoxy-1-naphthylthio group, or a 5,8-dimethoxy-2-naphthylthio group; and an arylthio group having not more than 12 carbon atoms in total, which is substituted with a halogen atom, such as a chlorophenylthio group, a dichlorophenylthio group, a trichlorophenylthio group, a bromophenylthio group, a dibromophenylthio group, an iodophenylthio group, a fluorophenylthio group, a chloronaphthylthio group, a bromonaphthylthio group, a difluorophenylthio group, a trifluorophenylthio group, a tetrafluorophenylthio group, or a pentafluorophenylthio group.

Examples of the substituted or unsubstituted carboxylic acid group include a linear or branched carboxylic acid group having 1 to 5 carbon atoms in total, such as a formic acid group, an acetic acid group, a trifluoroacetic acid group, a propionic acid group, an n-butyric acid group, an iso-butyric acid group, an n-pentanoic acid group, a 2-methylbutanoic acid group, or a pivalic acid group.

Examples of the substituted or unsubstituted sulfonic acid group include a methanesulfonic acid group, a trifluoromethanesulfonic acid group, and a toluenesulfonic acid group.

More preferable examples of Y will be shown below.

A more preferable example of Y may be, for example, a hydrogen atom.

Furthermore, examples of the halogen atom include a chlorine atom and a bromine atom.

Examples of the substituted or unsubstituted alkyl group include a linear or branched alkyl group having 1 to 3 carbon atoms in total, such as a methyl group, an ethyl group, or an iso-propyl group.

Examples of the substituted or unsubstituted aryl group include an aromatic hydrocarbon having not more than 12 carbon atoms in total, such as a phenyl group, a naphthyl group, or a cyclopentadienyl group;

an alkyl-substituted aryl group having not more than 9 carbon atoms in total, such as a 2-methylphenyl group, a 3-methylphenyl group, a 4-methylphenyl group, a 2-ethylphenyl group, a propylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, or a 3,6-dimethylphenyl group;

a monoalkoxyaryl group having not more than 9 carbon atoms in total, which is substituted with a substituted or unsubstituted alkyloxy group having not more than 3 carbon atoms, such as a 2-methoxyphenyl group, a 3-methoxyphenyl group, a 4-methoxyphenyl group, a 2-ethoxyphenyl group, or a propoxyphenyl group; and an aryl group having not more than 12 carbon atoms in total, which is substituted with a halogen atom, such as a chlorophenyl group, a dichlorophenyl group, a trichlorophenyl group, a bromophenyl group, a dibromophenyl group, a chloronaphthyl group, or a bromonaphthyl group.

Examples of the substituted or unsubstituted aralkyl group include an aralkyl group having not more than 9 carbon atoms in total, such as a benzyl group, a phenethyl group, or a phenyl propyl group.

Examples of the substituted or unsubstituted alkyloxy group include a linear or branched alkoxy group having 1 to 3 carbon atoms in total, such as a methoxy group, an ethoxy group, or an iso-propoxy group; and a cycloalkoxy group having 5 or 6 carbon atoms in total, such as a cyclopentyloxy group or a cyclohexyloxy group.

Examples of the substituted or unsubstituted alkylthio group include a linear or branched alkylthio group having 1 to 3 carbon atoms in total, such as a methylthio group, an ethylthio group, an n-propylthio group, or an iso-propylthio group;

a cycloalkylthio group having 5 or 6 carbon atoms in total, such as a cyclopentylthio group, or a cyclohexylthio group; and an alkylthioalkylthio group having 2 to 6 carbon atoms in total, such as a methylthioethylthio group, an ethylthioethylthio group, an n-propylthioethylthio group, an iso-propylthioethylthio group, an n-butylthioethylthio group, an iso-butylthioethylthio group, or a tert-butylthioethylthio group.

Examples of the substituted or unsubstituted aryloxy group include an unsubstituted or alkyl-substituted aryloxy group having not more than 9 carbon atoms in total, such as a phenyloxy group, a naphthyloxy group, a 2-methylphenyloxy group, a 3-methylphenyloxy group, a 4-methylphenyloxy group, a 2-ethylphenyloxy group, a propylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, or a 3,6-dimethylphenyloxy group;

a monoalkoxyaryloxy group having not more than 9 carbon atoms in total, which is substituted with a substituted or unsubstituted alkyloxy group having not more than 3 carbon atoms, such as a 2-methoxyphenyloxy group, a 3-methoxyphenyloxy group, a 4-methoxyphenyloxy group, a 2-ethoxyphenyloxy group, or a propoxyphenyloxy group; and an aryloxy group having not more than 12 carbon atoms in total, which is substituted with a halogen atom, such as a chlorophenyloxy group, a dichlorophenyloxy group, a trichlorophenyloxy group, a bromophenyloxy group, a dibromophenyloxy group, a chloronaphthyloxy group, or a bromonaphthyloxy group.

Examples of the substituted or unsubstituted arylthio group include an unsubstituted or alkyl-substituted arylthio group having not more than 9 carbon atoms in total, such as a phenylthio group, a 2-methylphenylthio group, a 3-methylphenylthio group, a 4-methylphenylthio group, a 2-ethylphenylthio group, a propylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, or a 3,6-dimethylphenylthio group;

a monoalkoxyarylthio group having not more than 9 carbon atoms in total, which is substituted with a substituted or unsubstituted alkyloxy group having not more than 3 carbon atoms, such as a 2-methoxyphenylthio group, a 3-methoxyphenylthio group, a 4-methoxyphenylthio group, a 2-ethoxyphenylthio group, or a propoxyphenylthio group; and an arylthio group having not more than 12 carbon atoms in total, which is substituted with a halogen atom, such as a chlorophenylthio group, a dichlorophenylthio group, a trichlorophenylthio group, a bromophenylthio group, a dibromophenylthio group, a chloronaphthylthio group, or a bromonaphthylthio group.

Examples of the substituted or unsubstituted carboxylic acid group include a linear or branched carboxylic acid group having 1 to 3 carbon atoms in total, such as a formic acid group, an acetic acid group, a trifluoroacetic acid group, a propionic acid group, an n-butyric acid group, or an iso-butyric acid group.

Examples of the substituted or unsubstituted sulfonic acid group include a methanesulfonic acid group and a trifluoromethanesulfonic acid group.

When Y does not form a ring, more specific examples of Y include an alkyl group having 1 to 3 carbon atoms, such as a methyl group, an ethyl group, a propyl group, or an isopropyl group;

a cyclopentadienyl group; and a linear or branched alkylthio group having 1 to 3 carbon atoms in total, which contains a sulfur atom that is directly bonded to the lanthanoid atom of M, such as a methylthio group, an ethylthio group, an n-propylthio group, or an isopropylthio group.

When Y is an alkyl group, Y for the formula (1) is preferably a methyl group.

Furthermore, when n–p is an integer of not less than 2, Y may be bonded with each other and form a cyclic structure with a lanthanoid atom M. That is, a plurality of Y's may be bonded to form a ring containing a lanthanoid atom M.

When a ring is formed, the alkyl chain that forms the ring may be a methylene group, an ethylene group or a propylene group, that is, an alkylene group having 1 to 3 carbon atoms. The alkyl chain that forms the ring is preferably an ethylene group. The ring containing a lanthanoid atom, M, is specifically a 4-membered ring to a 6-membered ring, and the atom that constitutes the ring may be M, which is a lanthanoid atom, and C (carbon).

In addition to the lanthanoid atom and C (carbon), the atom that constitutes the ring may also include, for example, S or O. In the case where the lanthanoid atom is a trivalent atom, and the ring contains S, specific examples of the divalent group that is bound to the lanthanoid atom include $-S(CH_2)_2S-$, $-S(CH_2)_3S-$, and $-S(CH_2)_2S(CH_2)_2S-$. When the ring containing a lanthanoid atom M contains O, specific examples of the divalent group that is bound to M include $-OC(O)C(O)O-$, and $-OC(O)CH_2C(O)O-$. It is thought that these compounds can be produced by, for example, allowing oxalic acid to be co-present when a salt of the lanthanoid atom M and a thietane compound are reacted.

As another embodiment of the metal thietane compound according to the invention, there is a compound in which a ligand coordinates with a metal atom M. That is, the metal thioetane compound represented by the formula (1) may further contain a coordination compound that binds to a metal atom through coordination bonding.

The coordination compound contains in the molecule a coordination functional group that coordinates to one or more metal atoms. Furthermore, as the coordination compound, for example, any compound having any structure capable of coordinating to the compound represented by the formula (1) can be used, but the coordination compound is preferably a compound that coordinates to metal through a heteroatom such as a nitrogen, oxygen, phosphorus or sulfur atom.

Specific compound examples of the ligand that coordinates through a nitrogen atom include ammonia and amine compounds such as ammonia, methylamine, ethylamine, propylamine, isopropylamine, dimethylamine, diethylamine, dipropylamine, diisopropylamine, trimethylamine, triethylamine, ethylenediamine, propylenediamine, dimethylethylenediamine, tetramethylethylenediamine, hydrazine, methylhydrazine, dimethylhydrazine, aniline, phenylhydrazine, o-phenylenediamine, hydroxylamine, cysteamine, aminoethanol, and glycine;.

pyridine compounds such as pyridine, 2,2'-bipyridine and 1,10-phenanthroline;

nitrogen heterocyclic compounds such as pyridazine, pyrimidine, purine, pyrazine, 1,8-naphthyridine, pyrazole and imidazole;

amide compounds such as dimethylformamide, and dimethylimidazolidinone; and nitrile compounds such as acetonitrile and propionitrile.

Specific compound examples of the ligand that coordinates through a phosphorus atom include phosphine compounds such as triphenylphosphine, trimethylphosphine, triethylphosphine, 1,2-bis(dimethylphosphino)ethane, and bis(dimethylphosphino)methane.

Specific compound examples of the ligand that coordinates through an oxygen atom include water and alcohol compounds such as water, methanol, ethanol, propanol, isopropanol, ethylene glycol, propylene glycol, and 1,3-propanediol;

ether compounds such as tetrahydrofuran, 1,4-dioxane, dimethoxyethane, and ethylene glycol monomethyl ether;

ketone compounds such as acetone and methyl ethyl ketone;

ester compounds such as ethyl acetate, methyl acetate, methyl formate and ethyl formate; and sulfoxide compounds and sulfone compounds such as dimethyl sulfoxide and sulfolane.

Specific compound examples of the ligand that coordinates through a sulfur atom include sulfide compounds such as dimethyl sulfide, diethyl sulfide, and tetrahydrothiophene, but are not intended to be limited to the exemplary compounds.

Among these exemplary coordination compounds, preferable examples include ammonia and amine compounds such as ammonia, ethylenediamine, tetramethylethylenediamine, and hydroxylamine;

pyridine compounds such as pyridine and 2,2'-bipyridine;

ether compounds such as tetrahydrofuran and dimethoxyethane; and the like.

More preferable examples include tetrahydrofuran and tetramethylethylenediamine.

Next, the compound represented by the formula (101) will be explained.

$R^2$, Y, p and n in the formula (101) have the same definitions as in the case of the formula (1), and $R^2$ and Y have been described above in connection with the formula (1).

$R^4$ may be a divalent group, and is preferably a substituted or unsubstituted alkylene group. Preferable examples of $R^4$ include substituted or unsubstituted alkylene groups having 1 to 20 carbon atoms, such as a methylene group, an ethylene group, a 1,2-dichloroethylene group, a trimethylene group, a tetramethylene group, a pentamethylene group, a cyclopentylene group, a hexamethylene group, a cyclohexylene group, a heptamethylene group, an octamethylene group, a nonamethylene group, a decamethylene group, an undecamethylene group, a dodecamethylene group, a tridecamethylene group, a tetradecamethylene group, and a pentadecamethylene group.

Among them, $R^4$ is preferably an ethylene group, from the viewpoint of refractive index, and solubility in a resin component.

B may be a divalent group containing a heteroatom from the viewpoint of the compatibility with a copolymerization monomer, and when B is a divalent organic group containing a heteroatom, B may be bonded with the organic groups of $R^2$ and $R^4$ through either a carbon atom or a heteroatom. Specifically, structures shown below are preferable.

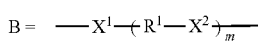
(111)

$X^1$, $X^2$, $R^1$ and m in the formula (111) have the same definitions as $X^1$, $X^2$, $R^1$ and m of the formula (1).

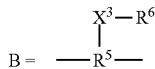
(112)

In the formula (112) above, $X^3$ represents a sulfur atom, an oxygen atom or an NH group; $R^5$ represents a trivalent organic group; and $R^6$ represents a monovalent organic group.

In the formula (112), the number of heteroatoms in B is preferably 1 to 5, from the viewpoint of refractive index, or solubility in a resin component. The number of heteroatoms is more preferably 1 to 2.

From the viewpoint of increasing the refractive index, $R^5$ is preferably a methine group, and $R^6$ is preferably an acetyl group. When $X^3$ is an NH group, the compound is represented by the following formula (113) (in the formula (113), $R^4$, $R^2$, M, p and n have the same definitions as in the formula (101)).

In the case of the following formula (113) or when B is represented by the formula (112), $R^2$ is particularly preferably a —$CH_2$(C=O)O— group or a —(C=O)O— group. Among them, $R^2$ is preferably a —(C=O)O— group from the viewpoint of increasing the refractive index.

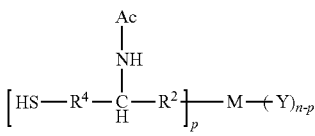
(113)

In the formula (113), Ac represents an acetyl group ($CH_3$—(C=O)—).

Furthermore, in the case of the formula (113) or when B is represented by the formula (112), it is preferable that p=n.

On the other hand, from the viewpoint of compatibility of the compound with copolymerization monomers, the structure of B is particularly preferably the formula (111), and in this case, the formula (101) is represented by the formula (102).

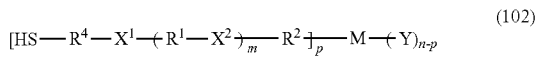
(102)

$X^1$, $X^2$, $R^1$, $R^2$, Y, M, m, p and n in the formula (102) have the same definitions as in the case of the formula (1). M represents a lanthanoid atom. $R^4$, $R^1$ and $R^2$ each independently represent a divalent organic group, and $R^4$ has the same definition as in the case of the formula (101) and is preferably a substituted or unsubstituted alkylene group.

Specifically, in the formula (102), it is preferable that $X^1$ and $X^2$ are sulfur atoms from the viewpoint of increasing the refractive index, and that m=0. It is more preferable that m=0 and $X^1$ is a sulfur atom. $R^2$ is preferably a —$CH_2$(C=O)O— group from the viewpoint of stability of the compound. For example, a compound represented by the following formula (103) is preferable.

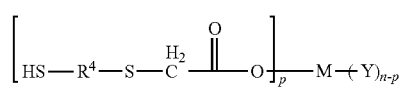
(103)

(In the formula (103), $R^4$, M, Y, n and p have the same definitions as $R^4$, M, Y, n and p of the formula (101).)

Furthermore, in the formulas (101), (102) and (103), it is preferable that n=p, and as discussed above, it is preferable that $R^4$ is an ethylene group. For example, a compound represented by the following formula (104) is preferable.

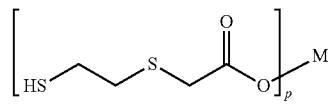
(104)

In the formula (101) (formulas (102) to (104) and (113)), M may be a lanthanoid atom, but among others, M is preferably an La atom from the viewpoint of increasing the Abbe number.

As explained in connection with the formulas (1) and (101), $R^2$, M, Y, p and n have the same definitions also for the formula (0), in addition to the formulas (1) and (101).

Next, the method for producing the compound represented by the above formula (0) will be described.

The compound represented by the formula (0) is typically produced by reacting a halide containing M as represented by the following formula (6), with a compound represented by the following formula (7).

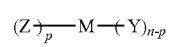
(6)

(In the formula (6), n, M, p and Y have the same definitions as n, M, p and Y of the formula (0); and Z represents a halogen atom.)

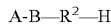
(7)

(In the formula (7), A, B and $R^2$ have the same definitions as A, B and $R^2$ of the formula (0).)

The compound represented by the formula (6) is available as a raw material for industrial use or a reagent for research use. The compound represented by the formula (7) is produced, for example, according to a method described in the Patent Document 2 (JP-A-2003-327583).

The reaction between the compound represented by the formula (6) and the compound represented by the formula (7) may be carried out without solvent, or may be carried out in the presence of a solvent inert to the reaction.

Such a solvent is not particularly limited so long as it is a solvent inert to the reaction, and examples include hydrocarbon-based solvents such as petroleum ether, hexane, benzene, toluene, xylene and mesitylene;

ether-based solvents such as diethyl ether, tetrahydrofuran, and diethylene glycol dimethyl ether;

ketone-based solvents such as acetone, methyl ethyl ketone and methyl isobutyl ketone;

ester-based solvents such as ethyl acetate, butyl acetate and amyl acetate;

chlorine-containing solvents such as methylene chloride, chloroform, chlorobenzene and dichlorobenzene;

aprotic polar solvents such as N,N-dimethylformamide, N,N-dimethylacetamide, N,N-dimethylimidazolidinone, and dimethyl sulfoxide;

sulfur-containing solvents such as tetrahydrothiophene, thiophene, sulfolane, trimethylene sulfide, diethyl sulfide, di-n-propyl sulfide, di-t-butyl sulfide, and bis(2-mercaptoethyl) sulfide; and water.

The temperature for the reaction between the compound represented by the formula (6) and the compound represented by the formula (7) is not particularly limited, but is usually in the range of equal to or higher than −78° C. to equal to or lower than 200° C., and preferably equal to or higher than −78° C. and equal to or lower than 100° C.

The reaction time is affected by the reaction temperature, but is usually from several minutes to 100 hours.

In the reaction between the compound represented by the formula (6) and the compound represented by the formula (7), the amounts used of the compound represented by the formula (6) and the compound represented by the formula (7) are not particularly limited, but usually, the amount used of the compound represented by the formula (7) with respect to one mole of the halogen atoms contained in the compound represented by the formula (6) is 0.01 moles to 100 moles. The amount used is preferably 0.1 moles to 50 moles, and more preferably 0.5 moles to 20 moles.

Upon carrying out the reaction between the compound represented by the formula (6) and the compound represented by the formula (7), in order to effectively perform the reaction, it is preferable to use a basic compound as a scavenger for hydrogen halide generated therein.

Examples of such a basic compound include inorganic bases such as sodium hydroxide, potassium hydroxide, lithium hydroxide, sodium carbonate, potassium carbonate, lithium carbonate, sodium bicarbonate, potassium bicarbonate, lithium bicarbonate, magnesium hydroxide, and calcium hydroxide; and Organic bases such as pyridine, triethylamine, dimethylaniline, diethylaniline, and 1,8-diazabicyclo[5,4,0]-7-undecene.

The compound represented by the formula (0) can also be produced according to a method other than the method using the metal halides. For example, the compound represented by the formula (0) can be produced by allowing the compound represented by the formula (7) to be reacted, using a metal carbonate, a metal acetate, a metal oxide or a metal amidate as a raw material.

Next, the polymerizable composition of the invention will be described.

The polymerizable composition of the invention includes the metal compound represented by the formula (0). This polymerizable composition is used as, for example, a material for optical components.

The polymerizable composition of the invention may contain one kind of compound as the compound represented by the formula (0), or may contain a plurality of compounds.

The metal compound represented by the formula (0) is a polymerizable compound. For this reason, the polymerizable compound in the polymerizable composition of the invention may be composed of the compound represented by the formula (0). Further, the polymerizable compound in the polymerizable composition of the invention may also contain another polymerizable compound in addition to the compound represented by the formula (0).

The content of the compound represented by the formula (0) occupying in the total weight of the polymerizable compound contained in the polymerizable composition of the invention is not particularly limited, but the content is usually not less than 1 wt %, and from the viewpoint of increasing the refractive index, the content is preferably not less than 30 wt %, more preferably not less than 50 wt %, and even more preferably not less than 70 wt %.

The components other than the compound represented by the formula (0) often cause a decrease in the refractive index of the resin utilizing the polymerizable composition. Therefore, from the viewpoint of obtaining a resin having a high refractive index, it is preferable to adjust the content of the compound represented by the formula (0) occupied in the total weight of the polymerizable compound, to be not less than 50 wt %.

The polymerizable composition according to the invention may further contain, as other components, one or more kind selected from the group consisting of, for example, an isocyanate compound, an active hydrogen compound, an epoxy compound, an epithio compound, and a thietane compound. In this manner, the mechanical properties and color of the resin obtainable by polymerizing the polymerizable composition may be further enhanced. Furthermore, when the other component is an active hydrogen compound, particularly a hydroxythiol, the amount added may be increased by enhancing the compatibility of the compound represented by the formula (0) with other copolymerization monomers.

Hereinafter, the various components will be described with reference to specific examples.

(Active Hydrogen Compound)

The active hydrogen compound used in the invention is a compound having active hydrogen (for example, a thiol group or a hydroxyl group), and is a compound other than the compound represented by the formula (0). The active hydrogen compound is specifically selected from a polyol compound, a polythiol compound and a hydroxythiol compound.

Among these, examples of the polyol compound include aliphatic polyols such as ethylene glycol, diethylene glycol, propylene glycol, dipropylene glycol, butylene glycol, neopentyl glycol, glycerin, trimethylolethane, trimethylolpropane, butanetriol, 1,2-methyl glycoside, pentaerythritol, dipentaerythritol, tripentaerythritol, sorbitol, erythritol, threitol, ribitol, arabinitol, xylytol, allitol, mannitol, dulcitol, iditol, glycol, inositol, hexanetriol, triglycerose, diglypherol, triethylene glycol, polyethylene glycol, tris(2-hydroxyethyl) isocyanurate, cyclobutanediol, cyclopentanediol, cyclohexanediol, cycloheptanediol, cyclooctanediol, cyclohexanedimethanol, hydroxypropyl cyclohexanol, tricyclo[5.2.1.0$^{2,6}$]decanedimethanol, bicyclo[4,3,0]-nonanediol, dicyclohexanediol, tricyclo[5,3,1,1]dodecanediol, bicyclo[4,3,0]nonanedimethanol, tricyclo[5,3,1,1]dodecane-diethanol, hydroxypropyltricyclo[5,3,1,1]dodecanol, spiro[3,4]octanediol, butylcyclohexanediol, 1,1'-bicyclohexylidenediol, cyclohexanetriol, maltitol, and lactose;

aromatic polyols such as dihydroxynaphthalene, trihydroxynaphthalene, tetrahydroxynaphthalene, dihydroxybenzene, benzenetriol, biphenyltetraol, pyrogallol, (hydroxynaphthyl)pyrogallol, trihydroxyphenanthrene, bisphenol A, bisphenol F, xylene glycol, di(2-hydroxyethoxy)benzene, bisphenol A-bis-(2-hydroxyethyl ether), tetrabromobisphenol A, and tetrabromobisphenol A-bis-(2-hydroxyethyl ether);

halogenated polyols such as dibromoneopentyl glycol; and polymeric polyols such as epoxy resin.

Other examples of the polyol compound include condensation reaction products of the polyols described above with organic acids such as oxalic acid, glutamic acid, adipic acid, acetic acid, propionic acid, cyclohexanecarboxylic acid, β-oxocyclohexanepropionic acid, dimeric acid, phthalic acid, isophthalic acid, salicylic acid, 3-bromopropionic acid, 2-bromoglycol, dicarboxycyclohexane, pyromellitic acid, butanetetracarboxylic acid, and bromophthalic acid;

addition reaction products of the polyol compounds with alkylene oxides such as ethylene oxide and propylene oxide;

addition reaction products of alkylenepolyamines with alkylene oxides such as ethylene oxide and propylene oxide; and bis-[4-(hydroxyethoxy)phenyl]sulfide, bis-[4-(2-hydroxypropoxy)phenyl]sulfide, bis-[4-(2,3-dihydroxypropoxy)phenyl]sulfide, bis-[4-(4-hydroxycyclohexyloxy)phenyl]sulfide, bis-[2-methyl-4-(hydroxyethoxy)-6-butylphenyl] sulfide, and compounds formed by adding, to these compounds, 3 molecules or less on the average of ethylene oxide and/or propylene oxide per hydroxyl group; and polyols containing sulfur atoms, such as di(2-hydroxyethyl) sulfide, 1,2-bis-(2-hydroxyethylmercapto)ethane, bis(2-hydroxyethyl) disulfide, 1,4-dithiane-2,5-diol, bis(2,3-dihydroxypropyl) sulfide, tetrakis(4-hydroxy-2-thiabutyl) methane, bis(4-hydroxyphenyl)sulfone (trade name: bisphenol S), tetrabromobisphenol S, tetramethylbisphenol S, 4,4'-thiobis(6-tert-butyl-3-methylphenol), and 1,3-bis(2-hydroxyethylthioethyl)-cyclohexane.

Examples of the monovalent thiol compound include aliphatic mercaptan compounds such as methylmercaptan, ethylmercaptan, propylmercaptan, butylmercaptan, octylmercaptan, dodecylmercaptan, tent-dodecylmercaptan, hexadecylmercaptan, octadecylmercaptan, cyclohexylmercaptan, benzylmercaptan, ethylphenylmercaptan, 2-mercaptomethyl-1,3-dithiolan, 2-mercaptomethyl-1,4-dithiane, 1-mercapto-2,3-epithiopropane, 1-mercaptomethylthio-2,3-epithiopropane, 1-mercaptoethylthio-2,3-epithiopropane, 3-mercaptothietane, 2-mercaptothietane, 3-mercaptomethylthiothietane, 2-mercaptomethylthiothietane, 3-mercaptoethylthiothietane, and 2-mercaptoethylthiothietane; aromatic mercaptan compounds such as thiophenol, and mercaptotoluene; and compounds containing a hydroxyl group in addition to a mercapto group, such as 2-mercaptoethanol and 3-mercapto-1,2-propanediol.

Examples of the polythiol compound include aliphatic polythiols such as methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, bicyclo[2,2,1] pepta-exo-cis-2,3-dithiol, 1,1-bis(mercaptomethyl) cyclohexane, thiomalic acid bis(2-mercaptoethyl ester), 2,3-dimercaptosuccinic acid (2-mercaptoethyl ester), 2,3-dimercapto-1-propanol (2-mercaptoacetate), 2,3-dimercapto-1-propanol (3-mercaptoacetate), diethylene glycol bis(2-mercaptoacetate), diethylene glycol bis(3-mercaptopropionate), 1,2-dimercaptopropyl methyl ether, 2,3-dimercaptopropyl methyl ether, 2,2-bis(mercaptomethyl)-1, 3-propanedithiol, bis(2-mercaptoethyl)ether, ethylene glycol bis(2-mercaptoacetate), ethylene glycol bis(3-mercaptopropionate), trimethylolpropane tris(2-mercaptoacetate), trimethylolpropane tris(3-mercaptopropionate), pentaerythritol tetrakis(2-mercaptoacetate), pentaerythritol tetrakis(3-mercaptopropionate), and 1,2-bis(2-mercaptoethylthio)-3-mercaptopropane);

aromatic polythiols such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl) benzene, 1,3-bis(mercaptoethyl)benzene, 1,4-bis(mercaptoethyl)benzene, 1,2-bis(mercaptomethyleneoxy)benzene, 1,3-bis(mercaptomethyleneoxy)benzene, 1,4-bis(mercaptomethyleneoxy)benzene, 1,2-bis(mercaptoethyleneoxy) benzene, 1,3-bis(mercaptoethyleneoxy)benzene, 1,4-bis (mercaptoethyleneoxy)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl) benzene, 1,3,5-tris(mercaptomethyl)benzene, 1,2,3-tris(mercaptoethyl)benzene, 1,2,4-tris(mercaptoethyl)benzene, 1,3, 5-tris(mercaptoethyl)benzene, 1,2,3-tris (mercaptomethyleneoxy)benzene, 1,2,4-tris (mercaptomethyleneoxy)benzene, 1,3,5-tris (mercaptomethyleneoxy)benzene, 1,2,3-tris (mercaptoethyleneoxy)benzene, 1,2,4-tris (mercaptoethyleneoxy)benzene, 1,3,5-tris (mercaptoethyleneoxy)benzene, 1,2,3,4-tetramercaptobenzene, 1,2,3,5-tetramercaptobenzene, 1,2,4, 5-tetramercaptobenzene, 1,2,3,4-tetrakis(mercaptomethyl) benzene, 1,2,3,5-tetrakis(mercaptomethyl)benzene, 1,2,4,5-tetrakis(mercaptomethyl)benzene, 1,2,3,4-tetrakis (mercaptoethyl)benzene, 1,2,3,5-tetrakis(mercaptoethyl) benzene, 1,2,4,5-tetrakis(mercaptoethyl)benzene, 1,2,3,4-tetrakis(mercaptoethyl)benzene, 1,2,3,5-tetrakis (mercaptomethyleneoxy)benzene, 1,2,4,5-tetrakis (mercaptomethyleneoxy)benzene, 1,2,3,4-tetrakis (mercaptoethyleneoxy)benzene, 1,2,3,5-tetrakis (mercaptoethyleneoxy)benzene, 1,2,4,5-tetrakis (mercaptoethyleneoxy)benzene, 2,2'-dimercaptobiphenyl, 4,4'-dimercaptobiphenyl, 4,4'-dimercaptobibenzyl, 2,5-toluenedithiol, 3,4-toluenedithiol, 1,4-naphthalenedithiol, 1,5-naphthalenedithiol, 2,6-naphthalenedithiol, 2,7-naphthalenedithiol, 2,4-dimethylbenzene-1,3-dithiol, 4,5-dimethylbenzene-1,3-dithiol, 9,10-anthracenedimethanethiol, 1,3-di(p-methoxyphenyl) propane-2,2-dithiol, 1,3-diphenylpropane-2,2-dithiol, phenylmethane-1,1-dithiol, and 2,4-di(p-mercaptophenyl) pentane;

halogen-substituted aromatic polythiols such as chlorine substitution products and bromine substitution products, such as 2,5-dichlorobenzene-1,3-dithiol, 1,3-di(p-chlorophenyl) propane-2,2-dithiol, 3,4,5-tribromo-1,2-dimercaptobenzene, and 2,3,4,6-tetrachloro-1,5-bis(mercaptomethyl)benzene;

polythiols containing heterocycles, such as 2-methylamino-4,6-dithiol-sym-triazine, 2-ethylamino-4,6-dithiol-sym-triazine, 2-amino-4,6-dithiol-sym-triazine, 2-morpholino-4,6-dithiol-sym-triazine, 2-cyclohexylamino-4,6-dithiol-sym-triazine, 2-methoxy-4,6-dithiol-sym-triazine, 2-phenoxy-4,6-dithiol-sym-triazine, 2-thiobenzeneoxy-4,6-dithiol-sym-triazine, and 2-thiobutyloxy-4,6-dithiol-sym-triazine;

aromatic polythiols containing sulfur atoms in addition to a mercapto group, such as 1,2-bis(mercaptomethylthio)benzene, 1,3-bis(mercaptomethylthio)benzene, 1,4-bis(mercaptomethylthio)benzene, 1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2, 4-tris(mercaptomethylthio)benzene, 1,3,5-tris(mercaptomethylthio)benzene, 1,2,3-tris(mercaptoethylthio)benzene, 1,2,4-tris(mercaptoethylthio)benzene, 1,3,5-tris(mercaptoethylthio)benzene, 1,2,3,4-tetrakis(mercaptomethylthio)benzene, 1,2,3,5-tetrakis(mercaptomethylthio)benzene, 1,2,4,5-tetrakis(mercaptomethylthio)benzene, 1,2,3,4-tetrakis (mercaptoethylthio)benzene, 1,2,3,5-tetrakis (mercaptoethylthio)benzene, 1,2,4,5-tetrakis (mercaptoethylthio)benzene, and nuclear alkylation products thereof;

bis(mercaptomethyl) sulfide, bis(mercaptoethyl) sulfide, bis(mercaptopropyl) sulfide, bis(mercaptomethylthio)methane, bis(2-mercaptoethylthio)methane, bis(3-mercaptopropyl)methane, 1,2-bis(mercaptomethylthio)ethane, 1,2-bis(2-mercaptoethylthio)ethane, 1,2-bis(3-mercaptopropyl)ethane, 1,3-bis(mercaptomethylthio)propane, 1,3-bis(2-mercaptoethylthio)propane, 1,3-bis(3-mercaptopropylthio)propane, 1,2,3-tris(mercaptomethylthio)propane, 1,2,3-tris(2-mercaptoethylthio)propane, 1,2,3-tris(3-mercaptopropylthio)propane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl) sulfide, 2,5-dimercapto-1,4-dithiane, bis (mercaptomethyl) disulfide, bis(mercaptoethyl) disulfide, bis (mercaptopropyl) disulfide, 1,5-dimercapto-3-thiapentane, and thioglycolic acid and mercaptopropionic acid esters thereof;

aliphatic polythiols containing sulfur atoms in addition to a mercapto group, such as hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxypropyl sulfide bis(2-mercaptoacetate), hydroxypropyl sulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), hydroxypropyl disulfide bis(2-mercaptoacetate), hydroxypropyl disulfide bis(3-mercaptopropionate), 2-mercaptoethyl ether bis(2-mercaptoacetate), 2-mercaptoethyl ether bis(3-mercaptopropionate), 1,4-dithiane-2,5-diol bis(2-mercaptoacetate), 1,4-dithiane-2,5-diol bis(3-mercaptopropionate), thioglycolic acid bis(2-mercaptoethyl ester), thiodipropionic acid bis(2-mercaptoethyl ester), 4,4-thiodibutyric acid bis(2-mercaptoethyl ester), dithioglycolic acid bis(2-mercaptoethyl ester), dithiodipropionic acid bis(2-mercaptoethyl ester), 4,4-dithiodibutyric acid bis(2-mercaptoethyl ester), thiodiglycolic acid bis(2,3-dimercaptopropyl ester), thiodipropionic acid bis(2,3-dimercaptopropyl ester), dithioglycolic acid bis(2,3-dimercaptopropyl ester), dithiodipropionic acid (2,3-dimercaptopropyl ester), 2,5-bis(mercaptomethyl)-1,4-dithiane, 4-mercaptomethyl-1,8-dimercapto-3,6-dithiaoctane, 4,8-dimercaptomethyl-1,11-dimercapto-3,6,9-trithiaundecane, and 4,7-dimercaptomethyl-1,11-dimercapto-3,6,9-trithiaundecane; and heterocyclic compounds containing sulfur atoms in addition to a mercapto group, such as 3,4-thiophenedithiol and 2,5-dimercapto-1,3,4-thiadiazole.

Examples of the hydroxythiol compound include 2-mercaptoethanol, 3-mercapto-1,2-propanediol, glycerin di(mercaptoacetate), 1-hydroxy-4-mercaptocyclohexane, 2,4-dimercaptophenol, 2-mercaptohydroquinone, 4-mercaptophenol, 3,4-dimercapto-2-propanol, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopropionate), pentaerythritol bis(3-mercaptopropionate), pentaerythritol tris(thioglycolate), pentaerythritol pentakis(3-mercaptopropionate), hydroxymethyltris(mercaptoethylthiomethyl) methane, 1-hydroxyethylthio-3-mercaptoethylthiobenzene, 4-hydroxy-4'-mercaptodiphenylsulfone, 2-(2-mercaptoethylthio) ethanol, dihydroxyethyl sulfide mono(3-mercaptopropionate), dimercaptoethane mono(salicylate), and hydroxyethylthiomethyltris(mercaptoethylthio) methane.

Furthermore, halogen substitution products such as chlorine substitution products and bromine substitution products, of these active hydrogen compounds may also be used. These can be used singly, or as mixtures of two or more kinds.

In the case of using a thiol compound as an active hydrogen compound, when the optical properties, particularly the Abbe number, of the obtainable resin are taken into consideration, it is preferable to select an aliphatic thiol compound rather than an aromatic thiol compound. Furthermore, when the demand for the optical properties, particularly the refractive index, is taken into consideration, it is even more preferable to select a compound having a sulfur atom in addition to a thiol group, such as a sulfide bond and/or a disulfide bond. From the viewpoint of increasing three-dimensional crosslinkability by taking into consideration the heat resistance of the obtainable resin, it is particularly preferable to select one or more of a thiol compound having a polymerizable group such as an epithio group or a thiethanyl group, or a compound having three or more thiol groups.

Preferable thiol compounds from this point of view include 3-mercaptothietane, 1-mercapto-2,3-epithiopropane, 1-mercaptomethylthio-2,3-epithiopropane, 1-mercaptoethylthio-2,3-epithiopropane, 2-mercaptothietane, 3-mercaptomethylthiothietane, 2-mercaptomethylthiothietane, 3-mercaptoethylthiothietane, 2-mercaptoethylthiothietane, 2,5-bis(mercaptomethyl)-1,4-dithiane, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1,1-tetrakis(mercaptomethyl)methane, 1,1,3,3-tetrakis (mercaptomethylthio)propane, 1,1,2,2-tetrakis(mercaptoethylthio)ethane, 4,6-bis(mercaptomethylthio)-1,3-dithiane, and 2-(2,2-bis(mercaptomethylthio)ethyl)-1,3-dithietane.

More preferable thiol compounds are 3-mercaptothietane, 4-mercaptomethyl-1,8-dimercapto-3,6-dithiaoctane, 2,5-bis (mercaptomethyl)-1,4-dithiane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1,1-tetrakis(mercaptomethyl)methane, 1,1,3,3-tetrakis (mercaptomethylthio)propane, 1,1,2,2-tetrakis(mercaptoethylthio)ethane, 4,6-bis(mercaptomethylthio)-1,3-dithiane, and 2-(2,2-bis(mercaptomethylthio)ethyl)-1,3-dithietane. In the case of selecting a divalent thiol compound, it is preferable to use a thiol compound having a polymerizable group and/or a trivalent or higher-valent thiol compound in mixture.

More specifically, the thiol compound is one or more kind selected from the group consisting of 3-mercaptothietane, 1,2-ethanedithiol, 4-mercaptomethyl-1,8-dimercapto-3,6-dithiaoctane, 4,8-dimercaptomethyl-1,11-dimercapto-3,6,9-trithiaundecane and 2,5-bis(mercaptomethyl)-1,4-dithiane.

The amount of these thiol compounds used is such that when the sum of the compound represented by the formula (0) and the thiol compound is taken as 100 wt %, if the amount of the thiol compound used is too small, the effects of improving color and enhancing mechanical strength may be small, which is not preferable. When the sum of the compound represented by the formula (0) and the thiol compound is taken as 100 wt %, if the amount of the thiol compound used is too large, a decrease in heat resistance may be significant, which is not preferable.

Therefore, the amount of the thiol compound used is such that when the sum of the compound represented by the formula (0) and the thiol compound is taken as 100 wt %, it is preferable to use 1 wt % to 50 wt %. More preferably, the amount of the thiol compound used is 1 wt % to 25 wt %, when the sum of the compound represented by the formula (0) and the thiol compound is taken as 100 wt %.

Furthermore, an isocyanate compound may be further incorporated into the polymerizable composition, in addition to the thiol compound. By adding an isocyanate compound, mechanical properties and the like may be further improved.

The isocyanate compound used herein is not particularly limited, but a polyisocyanate compound having a plurality of isocyanate groups is preferable, and a diisocyanate compound is more preferable. Specifically, suitable examples include hexamethylene diisocyanate, bis(isocyanatomethyl)cyclohexane, xylene diisocyanate, dicyclohexylmethane diisocyanate, toluene diisocyanate, 2,5-bis(isocyanatomethyl) bicyclo[2,2,1]-heptane, 2,6-bis(isocyanatomethyl) bicyclo[2,2,1]-heptane, and isophorone diisocyanate.

Furthermore, a reaction product obtainable by reacting a thiol compound with an isocyanate compound in advance, may also be added to the polymerization product.

(Isocyanate Compound)

The isocyanate compound used in the invention is a compound containing one or more isocyanate groups (NCO group) in the molecule. By adding an isocyanate compound, mechanical properties and the like may be further improved.

The isocyanate compound used herein is not particularly limited, but a polyisocyanate compound having a plurality of isocyanate groups is preferable, and a diisocyanate compound is more preferable. Specifically, suitable examples include hexamethylene diisocyanate, bis(isocyanatomethyl)cyclohexane, xylene diisocyanate, dicyclohexylmethane diisocyanate, toluene diisocyanate, 2,5-bis(isocyanatomethyl) bicyclo[2,2,1]-heptane, 2,6-bis(isocyanatomethyl) bicyclo[2,2,1]-heptane, and isophorone diisocyanate.

The amount of the isocyanate compound used in the invention may vary with the components in the resin composition and the amounts used of the various components. However, when the refractive index of the obtainable resin is taken into consideration, it is preferable that the isocyanate compound is contained in an amount not more than 25 wt % based on the total amount of the polymerizable composition of the invention. The amount used is more preferably not more than 23 wt %, and even more preferably not more than 20 wt %. When the color and mechanical strength of the obtainable resin are taken into consideration, the amount used is preferably not less than 2.5 wt %.

(Epoxy Compound)

An epoxy compound and an epithio compound contain one or more epoxy groups and epithio groups, respectively, in the molecule. Furthermore, these compounds are preferably compounds containing two or more in total of an epoxy group and/or an epithio group.

Among these, specific examples of the epoxy compound include a phenolic epoxy compound obtainable by a condensation reaction between a polyhydric phenol compound such as bisphenol A or bisphenol F, and an epihalohydrin compound (for example, bisphenol A glycidyl ether, bisphenol F glycidyl ether);

an alcohol-based epoxy compound obtainable by condensation of a polyhydric alcohol compound such as hydrogenated bisphenol A, hydrogenated bisphenol F or cyclohexanedimethanol, and an epihalohydrin compound (for example, hydrogenated bisphenol A glycidyl ether, hydrogenated bisphenol F glycidyl ether), and other alcohol-based epoxy compounds, such as ethylene glycol diglycidyl ether, neopentyl glycol diglycidyl ether, 1,4-cyclohexanedimethanol diglycidyl ether, and trimethylolpropane triglycidyl ether;

a glycidyl ester-based epoxy compound such as 3,4-epoxycyclohexylmethyl-3',4'-epoxycyclohexane carboxylate or 1,2-hexahydrophthalic acid diglycidyl ester; and an amine-based epoxy compound obtainable by condensation of a primary or secondary amine compound and an epihalohydrin compound (for example, isocyanuric acid triglycidyl ether). In addition to these, an aliphatic polyvalent epoxy compound, such as vinylcyclohexene diepoxide including 4-vinyl-1-cyclohexane diepoxide, may be used.

Specific compound examples of a sulfide group-containing epoxy compound and an ether group-containing epoxy compound include linear aliphatic 2,3-epoxypropylthio compounds such as bis(2,3-epoxypropyl) sulfide, bis(2,3-epoxypropyl) disulfide, bis(2,3-epoxypropylthio)methane, 1,2-bis(2,3-epoxypropylthio)ethane, 1,2-bis(2,3-epoxypropylthio)propane, 1,3-bis(2,3-epoxypropylthio)propane, 1,3-bis(2,3-epoxypropylthio)-2-methylpropane, 1,4-bis(2,3-epoxypropylthio)butane, 1,4-bis(2,3-epoxypropylthio)-2-methylbutane, 1,3-bis(2,3-epoxypropylthio)butane, 1,5-bis(2,3-epoxypropylthio)pentane, 1,5-bis(2,3-epoxypropylthio)-2-methylpentane, 1,5-bis(2,3-epoxypropylthio)-3-thiapentane, 1,6-bis(2,3-epoxypropylthio)hexane, 1,6-bis(2,3-epoxypropylthio)-2-methylhexane, 3,8-bis(2,3-epoxypropylthio)-3,6-dithiaoctane, 1,2,3-tris(2,3-epoxypropylthio)propane, 2,2-bis(2,3-epoxypropylthio)-1,3-bis(2,3-epoxypropylthiomethyl)propane, 2,2-bis(2,3-epoxypropylthiomethyl)-1-(2,3-epoxypropylthio)butane, 1,5-bis(2,3-epoxypropylthio)-2-(2,3-epoxypropylthiomethyl)-3-thiapentane, 1,5-bis(2,3-epoxypropylthio)-2,4-bis(2,3-epoxypropylthiomethyl)-3-thiapentane, 1-(2,3-epoxypropylthio)-2,2-bis(2,3-epoxypropylthiomethyl)-4-thiahexane, 1,5,6-tris(2,3-epoxypropylthio)-4-(2,3-epoxypropylthiomethyl)-3-thiahexane, 1,8-bis(2,3-epoxypropylthio)-4-(2,3-epoxypropylthiomethyl)-3,6-dithiaoctane, 1,8-bis(2,3-epoxypropylthio)-4,5-bis(2,3-epoxypropylthiomethyl)-3,6-dithiaoctane, 1,8-bis(2,3-epoxypropylthio)-4,4-bis(2,3-epoxypropylthiomethyl)-3,6-dithiaoctane, 1,8-bis(2,3-epoxypropylthio)-2,5-bis(2,3-epoxypropylthiomethyl)-3,6-dithiaoctane, 1,8-bis(2,3-epoxypropylthio)-2,4,5-tris(2,3-epoxypropylthiomethyl)-3,6-dithiaoctane, 1,1,1-tris[[2-(2,3-epoxypropylthio)ethyl]thiomethyl]-2-(2,3-epoxypropylthio)ethane, 1,1,2,2-tetrakis[[2-(2,3-epoxypropylthio)ethyl]thiomethyl]ethane, 1,11-bis(2,3-epoxypropylthio)-4,8-bis(2,3-epoxypropylthiomethyl)-3,6,9-trithiaundecane, 1,11-bis(2,3-epoxypropylthio)-4,7-bis(2,3-epoxypropylthiomethyl)-3,6,9-trithiaundecane, 1,11-bis(2,3-epoxypropylthio)-5,7-bis(2,3-epoxypropylthiomethyl)-3,6,9-trithiaundecane, and 1,5-bis(glycidylthio)-3-thiapentane;

cyclic aliphatic 2,3-epoxypropylthio compounds such as 1,3-bis(2,3-epoxypropylthio)cyclohexane, 1,4-bis(2,3-epoxypropylthio)cyclohexane, 1,3-bis(2,3-epoxypropylthiomethyl)cyclohexane, 1,4-bis(2,3-epoxypropylthiomethyl)cyclohexane, 2,5-bis(2,3-epoxypropylthiomethyl)-1,4-dithiane, 2,5-bis[[2-(2,3-epoxypropylthio)ethyl]thiomethyl]-1,4-dithiane, 2,5-bis(2,3-epoxypropylthiomethyl)-2,5-dimethyl-1,4-dithiane, and 3-(2,3-epoxypropylthio)thietane;

aromatic 2,3-epoxypropylthio compounds such as 1,2-bis(2,3-epoxypropylthio)benzene, 1,3-bis(2,3-epoxypropylthio)benzene, 1,4-bis(2,3-epoxypropylthio)benzene, 1,2-bis (2,3-epoxypropylthiomethyl)benzene, 1,3-bis(2,3-epoxypropylthiomethyl)benzene, 1,4-bis(2,3-epoxypropylthiomethyl)benzene, bis[4-(2,3-epoxypropylthio)phenyl]methane, 2,2-bis[4-(2,3-epoxypropylthio)phenyl]propane, bis[4-(2,3-epoxypropylthio)phenyl]sulfide, bis[4-(2,3-epoxypropylthio) phenyl]sulfone, and 4,4'-bis(2,3-epoxypropylthio)biphenyl;

monofunctional epoxy compounds such as ethylene oxide, propylene oxide, glycidol, and epichlorohydrin;

chain-like aliphatic 2,3-epoxypropyloxy compounds such as bis(2,3-epoxypropyl)ether, bis(2,3-epoxypropyloxy) methane, 1,2-bis(2,3-epoxypropyloxy)ethane, 1,2-bis(2,3-epoxypropyloxy)propane, 1,3-bis(2,3-epoxypropyloxy)propane, 1,3-bis(2,3-epoxypropyloxy)-2-methylpropane, 1,4-bis(2,3-epoxypropyloxy)butane, 1,4-bis(2,3-epoxypropyloxy)-2-methylbutane, 1,3-bis(2,3-epoxypropyloxy)butane, 1,5-bis(2,3-epoxypropyloxy)pentane, 1,5-bis(2,3-epoxypropyloxy)-2-methylpentane, 1,5-bis(2,3-epoxypropyloxy)-3-thiapentane, 1,6-bis(2,3-epoxypropyloxy)hexane, 1,6-bis(2,3-epoxypropyloxy)-2-methylhexane, 3,8-bis(2,3-epoxypropyloxy)-3,6-dithiaoctane, 1,2,3-tris(2,3-epoxypropyloxy)propane, 2,2-bis(2,3-epoxypropyloxy)-1,3-bis(2,3-epoxypropyloxymethyl)propane, 2,2-bis(2,3-epoxypropyloxymethyl)-1-(2,3-epoxypropyloxy)butane, 1,5-bis(2,3-epoxypropyloxy)-2-(2,3-epoxypropyloxymethyl)-3-thiapentane, 1,5-bis(2,3-epoxypropyloxy)-2,4-bis(2,3-epoxypropyloxymethyl)-3-thiapentane, 1-(2,3-epoxypropyloxy)-2,2-bis(2,3-epoxypropyloxymethyl)-4-thiahexane, 1,5,6-tris(2,3-epoxypropyloxy)-4-(2,3-epoxypropyloxymethyl)-3-thiahexane, 1,8-bis(2,3-epoxypropyloxy)-4-(2,3-epoxypropyloxymethyl)-3,6-dithiaoctane, 1,8-bis(2,3-epoxypropyloxy)-4,5-bis(2,3-epoxypropyloxymethyl)-3,6-dithiaoctane, 1,8-bis(2,3-epoxypropyloxy)-4,4-bis(2,3-epoxypropyloxymethyl)-3,6-dithiaoctane, 1,8-bis(2,3-epoxypropyloxy)-2,5-bis(2,3-epoxypropyloxymethyl)-3,6-dithiaoctane, 1,8-bis(2,3-epoxypropyloxy)-2,4,5-tris(2,3-epoxypropyloxymethyl)-3,6-dithiaoctane, 1,1,1-tris[[2-(2,3-epoxypropyloxy)ethyl]thiomethyl]-2-(2,3-epoxy propyloxy) ethane, 1,1,2,2-tetrakis[[2-(2,3-epoxypropyloxy)ethyl] thiomethyl]ethane, 1,11-bis(2,3-epoxypropyloxy)-4,8-bis(2,3-epoxypropyloxymethyl)-3,6,9-trithiaundecane, 1,11-bis (2,3-epoxypropyloxy)-4,7-bis(2,3-epoxypropyloxymethyl)-3,6,9-trithiaundecane, and 1,11-bis(2,3-epoxypropyloxy)-5,7-bis(2,3-epoxypropyloxymethyl)-3,6,9-trithiaundecane;

cyclic aliphatic 2,3-epoxypropyloxy compounds such as 1,3-bis(2,3-epoxypropyloxy)cyclohexane, 1,4-bis(2,3-epoxypropyloxy)cyclohexane, 1,3-bis(2,3-epoxypropyloxymethyl)cyclohexane, 1,4-bis(2,3-epoxypropyloxymethyl)cyclohexane, 2,5-bis(2,3-epoxypropyloxymethyl)-1,4-dithiane, 2,5-bis[[2-(2,3-epoxypropyloxy)ethyl]thiomethyl]-1,4-dithiane, and 2,5-bis(2,3-epoxypropyloxymethyl)-2,5-dimethyl-1,4-dithiane; and aromatic 2,3-epoxypropyloxy compounds such as 1,2-bis (2,3-epoxypropyloxy)benzene, 1,3-bis(2,3-epoxypropyloxy)benzene, 1,4-bis(2,3-epoxypropyloxy)benzene, 1,2-bis (2,3-epoxypropyloxymethyl)benzene, 1,3-bis(2,3-epoxypropyloxymethyl)benzene, 1,4-bis(2,3-epoxypropyloxymethyl)benzene, bis[4-(2,3-epoxypropyloxy)phenyl]methane, 2,2-bis[4-(2,3-epoxypropyloxy)phenyl]propane, bis[4-(2,3-epoxypropyloxy)phenyl]sulfide, bis[4-(2,3-epoxypropyloxy)phenyl]sulfone, and 4,4'-bis(2,3-epoxypropyloxy)biphenyl. However, the epoxy compound is not intended to be limited to the exemplary compounds.

Among the exemplary epoxy compounds, preferable examples include phenolic epoxy compounds such as bis(2,3-epoxypropyl) disulfide, 4-vinyl-1-cyclohexanediepoxide, bisphenol A glycidyl ether, and bisphenol F glycidyl ether;

alcohol-based epoxy compounds such as hydrogenated bisphenol A glycidyl ether, hydrogenated bisphenol F glycidyl ether, ethylene glycol diglycidyl ether, neopentyl glycol diglycidyl ether, 1,4-cyclohexanedimethanol diglycidyl ether, and trimethylolpropane triglycidyl ether;

glycidyl ester-based epoxy compounds such as 3,4-epoxycyclohexyl methyl-3',4'-epoxycyclohexanecarboxylate and 1,2-hexahydrophthalic acid diglycidyl ester; and amine-based epoxy compounds such as isocyanuric acid triglycidyl ether.

In addition to those, aliphatic polyhydric epoxy compounds such as vinylcyclohexene diepoxide may be mentioned.

More preferable examples of the epoxy compounds include bis(2,3-epoxypropyl) disulfide, 1,4-cyclohexanedimethanol diglycidyl ether, bisphenol A glycidyl ether, bisphenol F glycidyl ether, ethylene glycol diglycidyl ether, neopentyl glycol diglycidyl ether, trimethylolpropane triglycidyl ether, and isocyanuric acid triglycidyl ether. Even more preferable examples include 1,4-cyclohexanedimethanol diglycidyl ether and bisphenol F glycidyl ether.

(Epithio Compound)

Specific examples of the epithio compound include epithioethylthio compounds such as bis(1,2-epithioethyl) sulfide, bis(1,2-epithioethyl) disulfide, bis(epithioethylthio)methane, bis(epithioethylthio)benzene, bis[4-(epithioethylthio)phenyl]sulfide, and bis[4-(epithioethylthio)phenyl]methane;

chain-like aliphatic 2,3-epithiopropylthio compounds such as bis(2,3-epithiopropyl) sulfide, bis(2,3-epithiopropyl) disulfide, bis(2,3-epithiopropylthio)methane, 1,2-bis(2,3-epithiopropylthio)ethane, 1,2-bis(2,3-epithiopropylthio)propane, 1,3-bis(2,3-epithiopropylthio)propane, 1,3-bis(2,3-epithiopropylthio)-2-methylpropane, 1,4-bis(2,3-epithiopropylthio)butane, 1,4-bis(2,3-epithiopropylthio)-2-methylbutane, 1,3-bis(2,3-epithiopropylthio)butane, 1,5-bis(2,3-epithiopropylthio)pentane, 1,5-bis(2,3-epithiopropylthio)-2-methylpentane, 1,5-bis(2,3-epithiopropylthio)-3-thiapentane, 1,6-bis(2,3-epithiopropylthio)hexane, 1,6-bis(2,3-epithiopropylthio)-2-methylhexane, 3,8-bis(2,3-epithiopropylthio)-3,6-dithiaoctane, 1,2,3-tris(2,3-epithiopropylthio)propane, 2,2-bis(2,3-epithiopropylthio)-1,3-bis(2,3-epithiopropylthiomethyl)propane, 2,2-bis(2,3-epithiopropylthiomethyl)-1-(2,3-epithiopropylthio)butane, 1,5-bis(2,3-epithiopropylthio)-2-(2,3-epithiopropylthiomethyl)-3-thiapentane, 1,5-bis(2,3-epithiopropylthio)-2,4-bis(2,3-epithiopropylthiomethyl)-3-thiapentane, 1-(2,3-epithiopropylthio)-2,2-bis(2,3-epithiopropylthiomethyl)-4-thiahexane, 1,5,6-tris(2,3-epithiopropylthio)-4-(2,3-epithiopropylthiomethyl-3-thiahexane, 1,8-bis(2,3-epithiopropylthio)-4-(2,3-epithiopropylthiomethyl)-3,6-dithiaoctane, 1,8-bis(2,3-epithiopropylthio)-4,5-bis(2,3-epithiopropylthiomethyl)-3,6-dithiaoctane, 1,8-bis(2,3-epithiopropylthio)-4,4-bis(2,3-epithiopropylthiomethyl)-3,6-dithiaoctane, 1,8-bis(2,3-epithiopropylthio)-2,5-bis(2,3-epithiopropylthiomethyl)-3,6-dithiaoctane, 1,8-bis(2,3-epithiopropylthio)-2,4,5-tris(2,3-epithiopropylthiom ethyl)-3,6-dithiaoctane, 1,1,1-tris[[2-(2,3-epithiopropylthio)ethyl]thiomethyl]-2-(2,3-epithiopropylthio)ethane, 1,1,2,2-tetrakis[[2-(2,3-epithiopropylthio)ethyl]thiomethyl]ethane, 1,11-bis(2,3-epithiopropylthio)-4,8-bis(2,3-epithiopropylthiomethyl)-3,6,9-trithiaundecane, 1,11-bis(2,3-epithiopropylthio)-4,7-bis(2,3-epithiopropylthiomethyl)-3,6,9-trithiaundecane, and 1,11-bis(2,3-epithiopropylthio)-5,7-bis(2,3-epithiopropylthiomethyl)-3,6,9-trithiaundecane;

cyclic aliphatic 2,3-epithiopropylthio compounds such as 1,3-bis(2,3-epithiopropylthio)cyclohexane, 1,4-bis(2,3-epithiopropylthio)cyclohexane, 1,3-bis(2,3-epithiopropylthiomethyl)cyclohexane, 1,4-bis(2,3-epithiopropylthiomethyl)cyclohexane, 2,5-bis(2,3-epithiopropylthiomethyl)-1,4-dithiane, 2,5-bis[[2-(2,3-epithiopropylthio)ethyl]thiomethyl]-1,4-dithiane, and 2,5-bis(2,3-epithiopropylthiomethyl)-2,5-dimethyl-1,4-dithiane; aromatic 2,3-epithiopropylthio compounds such as 1,2-bis(2,3-epithiopropylthio)benzene, 1,3-bis(2,3-epithiopropylthio)benzene, 1,4-bis(2,3-epithiopropylthio)benzene, 1,2-bis(2,3-epithiopropylthiomethyl)benzene, 1,3-bis(2,3-epithiopropylthiomethyl)benzene, 1,4-bis(2,3-epithiopropylthiomethyl)benzene, bis[4-(2,3-epithiopropylthio)phenyl]methane, 2,2-bis[4-(2,3-epithiopropylthio)phenyl]propane, bis[4-(2,3-epithiopropylthio)phenyl]sulfide, bis[4-(2,3-epithiopropylthio)phenyl]sulfone, and 4,4'-bis(2,3-epithiopropylthio)biphenyl;

compounds having one epithio group, such as ethylene sulfide, propylene sulfide, mercaptopropylene sulfide, mercaptobutene sulfide, and epithiochlorohydrin;

chain-like aliphatic 2,3-epithiopropyloxy compounds such as bis(2,3-epithiopropyl)ether, bis(2,3-epithiopropyloxy)methane, 1,2-bis(2,3-epithiopropyloxy)ethane, 1,2-bis(2,3-epithiopropyloxy)propane, 1,3-bis(2,3-epithiopropyloxy)propane, 1,3-bis(2,3-epithiopropyloxy)-2-methylpropane, 1,4-bis(2,3-epithiopropyloxy)butane, 1,4-bis(2,3-epithiopropyloxy)-2-methylbutane, 1,3-bis(2,3-epithiopropyloxy)butane, 1,5-bis(2,3-epithiopropyloxy)pentane, 1,5-bis(2,3-epithiopropyloxy)-2-methylpentane, 1,5-bis(2,3-epithiopropyloxy)-3-thiapentane, 1,6-bis(2,3-epithiopropyloxy)hexane, 1,6-bis(2,3-epithiopropyloxy)-2-methylhexane, 3,8-bis(2,3-epithiopropyloxy)-3,6-dithiaoctane, 1,2,3-tris(2,3-epithiopropyloxy)propane, 2,2-bis(2,3-epithiopropyloxy)-1,3-bis(2,3-epithiopropyloxymethyl) propane, 2,2-bis(2,3-epithiopropyloxymethyl)-1-(2,3-epithiopropyloxy)butane, 1,5-bis(2,3-epithiopropyloxy)-2-(2,3-epithiopropyloxymethyl)-3-thiapentane, 1,5-bis(2,3-epithiopropyloxy)-2,4-bis(2,3-epithiopropyloxymethyl-3-thiapentane, 1-(2,3-epithiopropyloxy)-2,2-bis(2,3-epithiopropyloxymethyl)-4-thiahexane, 1,5,6-tris(2,3-epithiopropyloxy)-4-(2,3-epithiopropyloxymethyl)-3-thiahexane, 1,8-bis(2,3-epithiopropyloxy)-4-(2,3-epithiopropyloxymethyl)-3,6-dithiaoctane, 1,8-bis(2,3-epithiopropyloxy)-4,5-bis(2,3-epithiopropyloxymethyl)-3,6-dithiaoctane, 1,8-bis(2,3-epithiopropyloxy)-4,4-bis(2,3-epithiopropyloxymethyl)-3,6-dithiaoctane, 1,8-bis(2,3-epithiopropyloxy)-2,5-bis(2,3-epithiopropyloxymethyl)-3,6-dithiaoctane, 1,8-bis(2,3-epithiopropyloxy)-2,4,5-tris(2,3-epithiopropyloxymethyl)-3,6-dithiaoctane, 1,1,1-tris[[2-(2,3-epithiopropyloxy)ethyl]thiomethyl]-2-(2,3-epi thiopropyloxy)ethane, 1,1,2,2-tetrakis[[2-(2,3-epithiopropyloxy)ethyl]thiomethyl]ethane, 1,11-bis(2,3-epithiopropyloxy)-4,8-bis(2,3-epithiopropyloxymethyl)-3,6,9-trithiaundecane, 1,11-bis(2,3-epithiopropyloxy)-4,7-bis(2,3-epithiopropyloxymethyl)-3,6,9-trithiaundecane, and 1,11-bis(2,3-epithiopropyloxy)-5,7-bis(2,3-epithiopropyloxymethyl)-3,6,9-trithiaundecane;

cyclic aliphatic 2,3-epithiopropyloxy compounds such as 1,3-bis(2,3-epithiopropyloxy)cyclohexane, 1,4-bis(2,3-epithiopropyloxy)cyclohexane, 1,3-bis(2,3-epithiopropyloxymethyl)cyclohexane, 1,4-bis(2,3-epithiopropyloxymethyl)cyclohexane, 2,5-bis(2,3-epithiopropyloxymethyl)-1,4-dithiane, 2,5-bis[[2-(2,3-epithiopropyloxy)ethyl]thiomethyl]-1,4-dithiane, and 2,5-bis(2,3-epithiopropyloxymethyl)-2,5-dimethyl-1,4-dithiane; and aromatic 2,3-epithiopropyloxy compounds such as 1,2-bis(2,3-epithiopropyloxy)benzene, 1,3-bis(2,3-epithiopropyloxy)benzene, 1,4-bis(2,3-epithiopropyloxy)benzene, 1,2-bis(2,3-epithiopropyloxymethyl)benzene, 1,3-bis(2,3-epithiopropyloxymethyl)benzene, 1,4-bis(2,3-epithiopropyloxymethyl)benzene, bis[4-(2,3-epithiopropyloxy)phenyl]methane, 2,2-bis[4-(2,3-epithiopropyloxy)phenyl]propane, bis[4-(2,3-epithiopropyloxy)phenyl]sulfide, bis[4-(2,3-epithiopropyloxy)phenyl]sulfone, and 4,4'-bis(2,3-epithiopropyloxy)biphenyl, but the epithio compound is not limited to these exemplary compounds.

Among these exemplary compounds, preferable compounds include bis(1,2-epithioethyl) sulfide, bis(1,2-epithioethyl) disulfide, bis(2,3-epithiopropyl) sulfide, bis(2,3-epithiopropylthio)methane and bis(2,3-epithiopropyl) disulfide, and more preferable compounds include bis(1,2-epithioethyl) sulfide, bis(1,2-epithioethyl) disulfide, bis(2,3-epithiopropyl) sulfide, and bis(2,3-epithiopropyl) disulfide. Even more preferable compounds include bis(2,3-epithiopropyl) sulfide and bis(2,3-epithiopropyl) disulfide.

The amount of the epoxy compound and/or epithio compound used may vary with the structure of the components in the resin composition or the amount used, but when the refractive index of the obtainable resin is taken into consideration, a content equal to less than 25 wt % based on the total amount of the polymerizable composition of the invention is preferable. A content of not more than 23 wt % is more preferable, and a content of not more than 20 wt % is even more preferable. When the color and mechanical strength of the obtainable resin is taken into consideration, a content of not less than 2.5 wt % is preferable.

In regard to the epoxy compound and/or epithio compound, either one may be used alone, or both of the compounds can be used together, and the amount ratio is not particularly limited. Furthermore, a combination of a plurality of different epoxy compounds or a combination of a plurality of different epithio compounds, may also be used as the epoxy compound or as the epithio compound, respectively. However, in order to obtain a resin with a high refractive index, it is preferable to use an epithio compound.

When the polymerizable compound further contains an epoxy compound and/or an epithio compound, the content of the compound represented by the formula (0) occupied in the total weight of the polymerizable compound contained in the polymerizable composition of the invention, is not particularly limited, and is usually not less than 1 wt %. Furthermore, there is a tendency that as the content of the compound represented by the formula (0) (particularly, the formula (1)) increases, a material with a higher refractive index is obtained. Thus, the content is preferably not less than 30 wt %, more preferably not less than 50 wt %, and even more preferably not less than 70 wt %.

However, if the content of the compound represented by the formula (0) is too large, the content of the thiol compound and the content of the epoxy compound and/or epithio compound relatively decrease. Therefore, from the viewpoint of improving the color of the resin and suppressing a decrease in the mechanical strength, it is preferable to set the content of the compound represented by the formula (0) in the polymerizable composition at not more than 95 wt %.

Furthermore, when a thiol compound is used together with an epoxy compound and/or an epithio compound, the amount of the thiol compound used may vary with the structure of the compound used, and the structure or amount of the epoxy compound and/or epithio compound used. However, since the compound represented by the formula (0) yields a resin having a high refractive index, addition of the thiol compound generally means a decrease in the refractive index of the obtainable resin. Therefore, when the refractive index of the obtainable resin is taken into consideration, the content of the thiol compound based on the total amount of the polymerizable composition of the invention is preferably not more than 35 wt %. A content of not more than 30 wt % is more preferable, and a content of not more than 25 wt % is even more preferable. When the color and mechanical strength of the obtainable resin are taken into consideration, a content of not less than 2.5 wt % is preferable.

When a thiol compound is used together with an epoxy compound and/or an epithio compound, the ratio of the amount of the thiol compound used and the epoxy compound and/or epithio compound is such that the functional group ratio of the thiol groups in the thiol compound, and the epoxy groups and/or epithio groups in the epoxy compound and/or epithio compound (SH group/(epoxy group+epithio group)) is preferably not less than 0.7, from the viewpoint of the resin color. The functional group ratio is more preferably 0.9 to 5, and even more preferably 0.9 to 3. If this functional group ratio is too small, the mechanical strength of the obtainable resin may decrease, and if the functional group ratio is too large, heat resistance of the obtainable resin may decrease.

(Thietane Compound)

A thietane compound contains one or more thietanyl groups in the molecule. When the compound represented by the formula (0) has a thietanyl group, the thietane compound may be a non-metal thietane compound that does not contain a metal atom in the molecular structure, or may be a metal-thietane compound containing a metal atom in the molecular structure, so long as the thietane compound is a thietane compound other than the compound represented by the formula (0). Furthermore, a thietane compound having any structure can be used so long as, for example, the thietane compound is mutually soluble with the compound represented by the formula (0), but the thietane compound is preferably a compound containing two or more thietanyl groups in total.

Specific examples of the non-metal thietane compound include sulfide-based thietane compounds such as bisthietanyl sulfide, bis(thietanylthio)methane, and 3-(((thietanylthio)methylthio)methylthio)thietane; and polysulfide-based thietane compounds such as bisthietanyl disulfide, bisthietanyl trisulfide, bisthietanyl tetrasulfide, and bisthietanyl pentasulfide.

Specific examples of the metal-thietane compound include alkyl(thietanylthio)tin such as methylthiotris(thietanylthio) tin, ethylthiotris(thietanylthio)tin, propylthiotris(thietanylthio)tin, or isopropylthiotris(thietanylthio)tin;

bis(alkylthio)bis(thietanylthio)tin such as bis(methylthio) bis(thietanylthio)tin, bis(ethylthio)bis(thietanylthio)tin, bis (propylthio)bis(thietanylthio)tin, or bis(isopropylthio)bis (thietanylthio)tin;

alkylthio(alkylthio)bis(thietanylthio)tin such as ethylthio (methylthio)bis(thietanylthio)tin, methylthio(propylthio)bis (thietanylthio)tin, isopropylthio(methylthio)bis(thietanylthio)tin, ethylthio(propylthio)bis(thietanylthio)tin, ethylthio(isopropylthio)bis(thietanylthio)tin, or isopropylthio(propylthio)bis(thietanylthio)tin;

a bis(thietanylthio)cyclic dithiotin compound such as bis (thietanylthio)dithiastannetane, bis(thietanylthio)dithiastannolane, bis(thietanylthio)dithiastanninane, or bis(thietanylthio)trithiastannokane;

an alkyltin compound such as methyltris(thietanylthio)tin, dimethylbis(thietanylthio)tin, or butyltris(thietanylthio)tin; and a metal-thietane compound such as tetrakis(thietanylthio) tin, tetrakis(thietanylthio)germanium, or tris(thietanylthio) bismuth;

Among these exemplary compounds, it is preferable to select one or more kind selected from the group consisting of bisthietanyl sulfide, bisthietanyl disulfide, bisthietanyl tetrasulfide, bis(thietanylthio)methane, 3-(((thietanylthio)methylthio)methylthio)thietane, tetrakis(thietanylthio)tin, tris(thietanylthio)bismuth, and bis(thietanylthio)dithiastannolane.

Furthermore, among these exemplary compounds, more preferable compounds include bisthietanyl sulfide, bis(thietanylthio)methane, bisthietanyl disulfide, bisthietanyl tetrasulfide, bis(thietanylthio)dithiastannolane and tetrakis(thietanylthio)tin, and even more preferable compounds include bisthietanyl disulfide, bis(thietanylthio)dithiastannolane and tetrakis(thietanylthio)tin.

The amount of the thietane compound used may vary with the structure or amount of the compound used, but when the refractive index of the obtainable resin is taken into consideration, for example, a constitution containing the thietane compound in an amount not more than 25 wt %, preferably not more than 23 wt %, and more preferably not more than 20 wt %, based on the total amount of the polymerizable composition of the invention can be adopted. On the other hand, when the color and mechanical strength of the obtainable resin are taken into consideration, the amount of the thietane compound used is adjusted to, for example, not less than 2.5 wt %.

Specific examples of the combination with another polymerizable compound include combinations in which the thiol compound is one or more kind selected from the group consisting of 3-mercaptothietane, 1,2-ethanedithiol, 4-mercaptomethyl-1,8-dimercapto-3,6-dithiaoctane, 4,8-dimercaptomethyl-1,11-dimercapto-3,6,9-trithiaundecane and 2,5-bis (mercaptomethyl)-1,4-dithiane, while the epoxy compound is one or more kind selected from the group consisting of bis(2,3-epoxypropyl) disulfide, ethylene glycol diglycidyl ether, isocyanuric acid triglycidyl ether, neopentyl glycol diglycidyl ether, 1,4-cyclohexanedimethanol diglycidyl ether, trimethylolpropane triglycidyl ether, bisphenol F diglycidyl ether, bisphenol A diglycidyl ether, and 3,4-epoxycyclohexylmethyl-3',4'-epoxycyclohexane carboxylate; the epithio compound is one or more kind selected from the group consisting of bis(2,3-epithiopropyl) sulfide and bis(2,3-epithiopropyl) disulfide; and the thietane compound is one or more kind selected from the group consisting of bisthietanyl disulfide, bisthietanyl tetrasulfide, bis(thietanylthio)methane and 3-(((thietanylthio)methylthio)methylthio)thietane. In this case, the polymerizable composition may contain tetrakis (thietanylthio)tin, tris(thietanylthio)bismuth, or bis(thietanylthio)dithiastannolane.

In the polymerizable composition, the contents of the thiol compound, epoxy compound, epithio compound and thietane compound with respect to the compound represented by the formula (0) may be preferable if the content of the epoxy compound is small, and the contents of the thiol compound, epithio compound and thietane compound are large, from the viewpoint of the refractive index. Also, from the viewpoint of the resin color, it may be preferable if the content of the thiol compound is large.

In the polymerizable composition, the sum of the thiol compound, epoxy compound, epithio compound and thietane compound with respect to 100 wt % of the sum of the compound represented by the formula (0), thiol compound, epoxy compound, epithio compound and thietane compound is, for example, 1 wt % to 50 wt %.

The other polymerizable compound contained in the polymerizable composition according to the invention may be various known polymerizable monomers or polymerizable oligomers, and examples include (meth) acrylic acid ester compounds, vinyl compounds and oxetane compounds.

The polymerizable composition of the invention may further contain, as necessary, a known, commonly used polymerization catalyst in order to adjust the rate of polymerization.

The polymerizable composition of the invention may contain a bluing agent, if necessary. The bluing agent has an absorption band in the wavelength region ranging from orange to yellow in the visible light region, and has a function of adjusting the color of the resin. More specifically, the bluing agent contains substances exhibiting colors ranging from blue to violet.

The bluing agent used in the polymerizable composition of the invention is not particularly limited, and specific examples include a dye, a fluorescent whitening agent, a fluorescent pigment, and an inorganic pigment. However, the bluing agent is appropriately selected from among those that can be used as bluing agents, in accordance with the properties required of lenses or resin color. These bluing agents may be used individually, or may be used in a combination of two or more kinds.

Among these bluing agents, a dye is preferable from the viewpoint of the solubility in the polymerizable composition and from the viewpoint of the transparency of the obtainable resin. Among dyes, a dye containing at least one kind of dyes selected from blue dyes and violet dyes is preferable, but in some cases, a mixture of dyes of different colors may also be used. For example, dyes of blue series or violet series, as well as of grey dyes, brown dyes, red dyes or orange dyes can be used. Specific examples of the combination of these bluing agents include combinations of blue dyes and red dyes, and combinations of violet dyes and red dyes may be mentioned.

From the viewpoint of the absorption wavelength, a dye having a maximum absorption wavelength 520 nm to 600 nm is preferable, and a dye having a maximum absorption wavelength 540 nm to 580 nm is more preferable.

From the viewpoint of the structure of the compound, an anthraquinone-based dye is preferable.

Specific examples of the dye include "PS Blue RR", "PS Violet RC", "PET Blue 2000", "PS Brilliant Red HEY", and "MLP RED V-1" (trade names of DyStar Japan, Ltd.).

The amount of the bluing agent used may vary according to the type of the monomer, the presence or absence of the use of various additives, the type or amount of the additives used, the polymerization method, and the polymerization conditions, but in general, the bluing agent is used at a proportion 0.001 ppm to 500 ppm, preferably 0.005 ppm to 100 ppm, and more preferably 0.01 ppm to 10 ppm, based on the total amount of the monomer used, that is, the total weight of the polymerizable compound contained in the polymerizable composition. If the amount of the bluing agent added is too large, the entire lens becomes excessively bluish, which may not be preferable, and if the amount is too small, the color improving effects are not sufficiently exhibited, which may not be preferable.

The method of addition of the bluing agent is not particularly limited, and it is preferable to add the bluing agent into the monomer system in advance. However, as the method of addition, various methods such as a method of dissolving a bluing agent in the monomer, or a method of preparing a master solution containing a high concentration of a bluing agent, diluting the master solution with the monomer used or another additive, and adding the dilution, can be employed.

For the purpose of improving the resin or improving the handlability, such as for further adjustment of the optical properties such as the refractive index and Abbe number of the resin formed by curing the polymerizable composition, adjustment of various properties such as color, lightfastness, weather resistance, heat resistance, impact resistance, hardness, specific gravity, coefficient of linear expansion, polymerization shrinkage, water absorbability, moisture absorbability, chemical resistance and viscoelasticity, adjustment of transmissivity or transparency, and adjustment of the viscosity of the polymerizable composition and the handlability of the storage or transportation method, subjecting the polymerizable composition of the invention to those techniques and operations generally used upon synthesizing an organic compound, such as purification, washing, heat retention, cold retention, filtration or treatment under reduced pressure, or adding known compounds as stabilizers or resin modifying agents, may be preferable for the purpose of obtaining a satisfactory resin. Examples of the agent for enhancing stability such as long-term storage stability, polymerization stability or thermal stability, include compounds such as a polymerization retardant, a polymerization inhibitor, a deoxidant, and an antioxidant.

Purification of the polymerizable composition is a technique used for improving the transparency of the resin obtainable by curing, for improving the color, or for increasing the purity. In order to purify the polymerizable composition of the invention, any known technique, for example, recrystallization, column chromatography (silica gel method, activated carbon method, ion-exchange resin method or the like) or extraction, may be carried out at any time, and it is preferable to improve transparency or color of the resin obtainable by curing the obtainable composition by purifying the composition in a general manner.

The method of washing the polymerizable composition is a technique used for improving the transparency of the resin obtainable by curing or improving the color, and there may be mentioned a method of washing the polymerizable composition with a polar and/or a non-polar solvent at a time upon synthesizing the polymerization composition and taking out the product or at a time after taking out the product after synthesis, and removing or reducing a substance that inhibits transparency of the resin, for example, an inorganic salt used or side-produced upon the synthesis of the polymerizable composition, for example, an ammonium salt. The solvent to be used cannot be defined simply by the polymerizable composition to be washed itself, or the polarity of the solution containing the polymerizable composition; however, a solvent is preferable that is capable of dissolving those components desired to be removed, and is difficult to mutually dissolve the polymerizable composition to be washed itself or a solution containing the polymerizable composition. One kind of solvent may be used, or two or more kinds of solvents may be used as a mixture. Here, the components to be removed may vary in accordance with the purpose or use, but it is preferable to reduce as much as possible the components to be removed, and when the content of such components is adjusted to be usually not more than 5000 ppm, more preferably not more than 1000 ppm, good results may be obtained.

The methods for cold retention or heart retention of the polymerizable composition, or filtering the polymerizable composition are techniques used to improve transparency of the resin obtainable by curing or to improve the color, but it is usual to carry out such treatments upon taking out the product after synthesizing the polymerization composition or after taking out the product after synthesizing the polymerization composition. The method for cold retention or heart retention may be, for example, a method of heating and dissolving the polymerizable composition to an extent of not impairing the performance of the polymerizable composition and the resin formed by curing the polymerizable composition, when the polymerizable composition crystallizes during storage and becomes poorly handlable. The temperature range for heating or the method of heating and dissolving cannot be defined simply by the structure of the compounds constituting the polymerizable composition to be handled, but there may be mentioned a method which is carried out at a temperature of freezing point+50° C. or less, and preferably freezing point+20° C. or less, and which dissolves by mechanically stirring with an apparatus capable of stirring, or by agitating the internal liquid by bubbling a gas that is inert to the composition. The cold retention is usually carried out for the purpose of increasing the storage stability of the polymerizable composition, but for example, when the melting point of the polymerizable composition is high, it is preferable to take the storage temperature into consideration so as to enhance the handlability after crystallization. The cold retention temperature cannot be defined simply by the structure of the compounds constituting the polymerizable composition handled, or storage stability; however, it is usually necessary to store the polymerizable composition at or below the temperature where the stability of the polymerizable composition of the invention can be maintained.

When the polymerizable composition of the invention is a polymerizable composition used for optical applications, very high transparency is required, and therefore, it is desirable to filter the polymerizable composition through a filter having a small pore diameter. The pore diameter of the filter used herein is usually 0.05 µm to 10 µm, but upon considering operability or performance, the pore diameter is preferably 0.05 µm to 5 µm, and more preferably 0.1 µm to 5 µm. The polymerizable composition of the invention is not an exception, and good results are often obtained through filtration. With regard to the temperature for filtration, more preferable results may be obtained when filtration is performed at a low temperature near the freezing point, but in the case where congelation is likely to occur during filtration, filtration may be performed at a temperature which does not bring about impediment in the filtration operation.

The treatment under reduced pressure is a technique that is generally carried out to remove any solvent or dissolved gas that decreases the performance of the resin formed by curing the polymerizable composition, or a foul odor. Since a dissolved solvent may generally cause a decrease in the refractive index or a decrease in the heat resistance of the obtainable resin, it is desirable to remove the dissolved solvent as far as possible. The acceptable level of the dissolved solvent cannot be defined simply by the structure of the compounds constituting the polymerizable composition to be handled or the structure of the dissolved solvent; however, it is preferable to maintain the level usually at 1% or more, and more preferably 5000 ppm or more. The dissolved gas is preferably removed, from the viewpoint of suppressing inhibition of polymerization and from the viewpoint of suppressing incorporation of air bubbles into the obtainable resin. Particularly, for a gas in the sense of moisture, such as water vapour, it is desirable to remove the gas particularly by bubbling with a dry gas. The dissolved amount can be set up in accordance with the structure of the compounds constituting the polymerizable composition, and the properties, structure and type of the dissolved gas.

A representative method for producing the polymerizable composition according to the invention may be a method of using a compound represented by the formula (0) together with those other various polymerizable compounds mentioned above, as necessary, adding a polymerization catalyst according to necessity, and then mixing and dissolving the mixture.

Since the obtained polymerizable composition contains the compound represented by the formula (0), a decrease in the Abbe number can be suppressed while a high refractive index of the resin is realized. Accordingly, the polymerizable composition is useful as a raw material monomer composition for transparent resin having a high refractive index and a high Abbe number.

The obtained polymerizable composition can be usually polymerized according to a known method of polymerizing a thietanyl group-containing compound, and cured.

The type or amount of the polymerization catalyst for obtaining a cured resin, and the type or ratio of the monomers are set up based on the structure of the compounds constituting the polymerizable composition.

In order to perform molding by curing the polymerizable composition of the invention, in accordance with a purpose, various substances may be added thereto, such as a stabilizer, a resin modifying agent, a chain extending agent, a crosslinking agent, a photostabilizer represented by the HALS series, an ultraviolet absorbent represented by the benzotriazole series, an antioxidant represented by the hindered phenol series, a coloration preventing agent, a filler, an external releasing agent represented by the silicone series, or an internal releasing agent represented by a surfactant such as an acidic phosphoric acid ester, a quaternary ammonium salt or a quaternary phosphonium salt, and an adhesiveness enhancing agent, as in the case of known molding methods. Here, the internal releasing agent also includes a catalyst exhibiting a releasing effect among the various catalysts described above.

The amount added of the various additives that can be added may vary with the type, structure and effects of the respective additives and cannot be defined simply. However, the additives are usually used in an amount in the range 0.001 wt % to 10 wt %, and preferably in the range 0.01 wt % to 5 wt %, based on the total weight of the polymerizable composition. When the additives are used in these ranges, a resin that has been more satisfactorily cured can be produced, and the transparency and optical properties of the obtainable resin may become more satisfactory.

A resin is obtained by polymerizing the polymerizable composition. In regard to the method of polymerization, various known methods used upon producing a plastic lens may be used, but a representative method may be cast polymerization.

In order to cast polymerize the polymerizable composition of the invention, the polymerizable composition is subjected to an defoaming treatment under reduced pressure or filter filtration as necessary, subsequently injected into a mold for molding, and polymerized by heating as necessary. In this case, it is preferable to polymerize the polymerizable composition by slowly heating from low temperature to high temperature.

The mold for molding described above is composed of, for example, two parts of mirror-surface polished molds, through a gasket formed from polyethylene, an ethylene vinyl acetate copolymer, polyvinyl chloride or the like, disposed therebetween. A representative combination of the molds is a combination of glass and glass, and in addition to those, there may be mentioned a combination of glass and a plastic plate, a combination of glass and a metal plate, and the like, but the molds are not limited to these. The molds for molding may be such that two parts of molds are fixed with a tape such as a polyester adhesive tape. If necessary, the molds may also be subjected to a known treatment method such as a releasing treatment.

In the case of performing cast polymerization, the polymerization temperature is affected by the polymerization conditions such as the type of the polymerization initiator, and thus is not limited. However, the polymerization temperature is usually equal to or higher than −50° C. and equal to or lower than 200° C., preferably equal to or higher than −20° C. and equal to or lower than 170° C., and more preferably equal to or higher than 0° and equal to or lower than 150° C.

The polymerization time is affected by the polymerization temperature, but is usually 0.01 hours to 200 hours, and preferably 0.05 hours to 100 hours. Furthermore, if necessary, it is also possible to perform polymerization by combining several temperatures by maintaining a constant temperature, or increasing the temperature or decreasing the temperature.

The polymerizable composition of the invention can also be polymerized by being irradiated with an active energy ray such as an electron beam, ultraviolet rays or visible light. In this case, if necessary, a radical polymerization catalyst or a cationic polymerization catalyst, which initiates polymerization by means of an active energy ray, is used.

The obtained resin may be subjected to an annealing treatment as necessary, after curing. Furthermore, if necessary, the resin may be subjected to various known physical or chemical treatments such as surface polishing, antistatic treatment, hard coating treatment, non-reflective coating treatment, staining treatment and photochromic treatment (for example, treatment for forming photochromic lens), for the purpose of prevention of reflection, impartation of high hardness, enhancement of abrasion resistance, impartation of antifog properties, or impartation of stylishness.

The resin obtainable by polymerizing the polymerizable composition of the invention has high transparency, good heat resistance, mechanical strength and a high refractive index. Thus, the resin is useful as a resin used in optical components, for example, plastic lenses.

Examples of the optical components include various plastic lenses such as spectacle lenses for sight correction, lenses for image capture devices, Fresnel lenses for liquid crystal projectors, lenticular lenses, and contact lenses;
encapslating materials for light emitting diodes (LED);
light waveguides;
optical adhesives used in the bonding of optical lenses or light waveguides;
antireflective films used in optical lenses; and
transparent coatings or transparent substrates used in liquid crystal display device members such as substrates, light guide panels, films and sheets.

The invention is not intended to be limited to the exemplary embodiments described above, and modifications, improvements and the like to the extent that the purpose of the invention can be achieved, are included in the invention.

EXAMPLES

Hereinafter, the invention will be more specifically described with reference to Examples, but the invention is not intended to be limited to these Examples.

Reference Preparation Example 1

3-Thietanol was synthesized according to the method described in Patent Document 2 (Japanese Laid-open patent publication No. 2003-327583). 3-Mercaptothietane was further synthesized using the 3-thietanol thus obtained.

That is, 190 g (2.50 moles) of thiourea, 253 g of 35 wt % aqueous hydrochloric acid, and 250 g of water were added into a reactor equipped with a stirring device and a thermometer, and the mixture was stirred to obtain a reaction mixture. While stirring the reaction mixture, 156 g (1.73 moles) of 3-thietanol was added dropwise to the reaction mixture over one hour. After completion of the dropwise addition, the reaction mixture was allowed to react by stirring at 30° C. for 24 hours, and then 177 g of 24 wt % aqueous ammonia was added dropwise thereto over one hour. After carrying out the reaction for 15 hours at 30° C., the reaction mixture was left to stand, and the organic layer (lower layer) was taken out to obtain 134 g of a crude product. The crude product thus obtained was distilled under reduced pressure, and a fraction having a boiling point of 40° C./106 Pa was collected. Thus, the target product, 3-mercaptothietane, was obtained as a colorless transparent liquid.

Reference Preparation Example 2

In the present Example, synthesis of thietanylthioacetic acid (compound represented by the following formula (8)) was carried out.

29.2 g of 3-mercaptothietane (0.27 moles: compound shown in Reference Preparation Example 1) was dispersed in 50 g of pure water, and the dispersion was cooled to 10° C. Subsequently, a solution prepared by dissolving 19.5 g of potassium hydroxide (0.30 moles: commercially available product (manufactured by Wako Pure Chemical Industries, Ltd.), purity 85%) in 50 g of pure water was added dropwise to the dispersion over 30 minutes. Furthermore, an aqueous solution prepared by dissolving 25.4 g of chloroacetic acid (0.27 moles: commercially available product (manufactured by Wako Pure Chemical Industries, Ltd.)) in 100 g of water, and neutralizing the solution by adding 14.3 g of sodium carbonate (0.14 moles: commercially available product (manufactured by Wako Pure Chemical Industries, Ltd.)) thereto, was added dropwise to the mixture over one hour. The resulting mixture was stirred for 4 hours. Thereafter, 50 g of 36% hydrochloric acid was added dropwise thereto, and the mixture was extracted using 200 g of ethyl acetate and separated. The organic layer was washed two times with 100 g of water, and further washed with 100 g of saturated saline. After separating, magnesium sulfate was added to the organic layer, and the organic layer was stirred, dried and filtered to remove salts. Then, ethyl acetate was distilled off with a rotary evaporator. Subsequently, while nitrogen was bubbling, pressure was reduced with a vacuum pump to distill off ethyl acetate in the oily product. Thus, 40.5 g of the target product, thietanylthioacetic acid, was obtained. The yield was 91%.

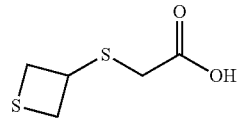

(8)

The identification data of the obtained compound are shown below.

$^1$H-NMR (solvent: DMSO, internal standard substance: TMS) δ: 3.24 (2H), 3.33 (2H), 3.37 (2H), 4.50 (1H), 12.63 (1H).

$^{13}$C-NMR (solvent: DMSO) δ: 32.4, 33.7, 39.5, 171.6.

IR (Universal ATR method): 3115, 1688, 1414, 1368, 1238, 1167, 1139, 856, 671, 653 cm$^{-1}$.

FD-MS: m/e164 (M$^+$).

Example 1

In the present Example, synthesis of lanthanum(III) tris(thietanylthioacetate) (compound represented by the following formula (9)) was carried out.

To a solution prepared by adding 32.8 g of pure water to 32.8 g (0.20 moles) of thietanylthioacetic acid synthesized in the Reference Preparation Example 2, and stirring and dispersing the mixture, 3.3 g of lanthanum oxide (0.01 moles: commercially available product (manufactured by Wako Pure Chemical Industries, Ltd.)) was added, and the mixture was stirred for 12 hours to allow the mixture to react. This solution was filtered to remove the insoluble matter, and the filtrate was poured into 200 g of ethanol and stirred to allow crystallization. The precipitated white solids were collected by filtration and washed with ethanol. The solids were dried under reduced pressure, and thus 10.8 g of the target product, lanthanum(III) tris(thietanylthioacetate), was obtained. The yield was 86%.

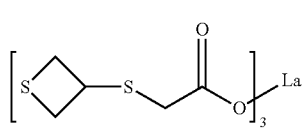

(9)

The identification data of the obtained compounds are shown below.

$^1$H-NMR (solvent: DMSO, internal standard substance: TMS) δ: 3.14 (6H), 3.25 (6H), 3.38 (6H), 4.53 (3H).

$^{13}$C-NMR (solvent: DMSO, internal standard substance: TMS) δ: 33.7, 35.1, 42.3, 178.6.

IR (Universal ATR method): 1540, 1383, 1221, 1167, 948, 893, 787, 700, 651, 586 $cm^{-1}$.

Elemental analysis: Calculated value La: 22.1%, Measured value La: 23.3%.

Example 2

In the present Example, synthesis of barium(II) bis(thietanylthioacetate) (compound represented by the following formula (10)) was carried out.

To a solution prepared by adding 8.2 g of pure water to 8.2 g (0.05 moles) of thietanylthioacetic acid synthesized in the Reference Preparation Example 2, and stirring and dispersing the mixture, 3.2 g of barium hydroxide (0.01 moles: commercially available product (manufactured by Wako Pure Chemical Industries, Ltd.)) was added, and the mixture was stirred for 12 hours to allow the mixture to react. This solution was filtered to remove the insoluble matter, and the filtrate was poured into 500 g of ethanol and cooled to allow crystallization. The precipitated white solids were collected by filtration and washed with ethanol. The solids were dried under reduced pressure, and thus 1.9 g of the target product, barium (II) bis(thietanylthioacetate), was obtained. The yield was 42%.

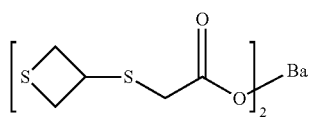

(10)

The identification data of the obtained compounds are shown below.

$^1$H-NMR (solvent: DMSO, internal standard substance: TMS) δ: 3.02 (4H), 3.20 (4H), 3.35 (4H), 4.48 (2H).

$^{13}$C-NMR (solvent: DMSO, internal standard substance: TMS) δ: 33.7, 36.2, 42.3, 174.4.

IR (Universal ATR method): 1565, 1390, 1225, 1173, 898, 777, 674, 440 $cm^{-1}$.

Elemental analysis: Calculated value Ba: 29.6%, Measured value Ba: 30.0%.

(Preparation of Polymerizable Composition and Production of Cured Resin Product by Polymerization of the Composition)

In the following Examples, polymerizable compositions were prepared using the thietane compounds produced in the above Preparation Examples or Examples, and these compositions were cured by polymerization to obtain resins.

The properties of the obtained resins or optical components (lenses) were evaluated by the methods shown below.

External appearance: Transparency was checked by visual inspection.

Refractive index, Abbe number: Measured at 20° C. using a Pulfrich refractometer.

Example 3

1.5 g of the compound produced in the Reference Preparation Example 2 was weighed in a glass beaker, and 0.5 g of the compound produced in Example 1 was added thereto, under room temperature (25° C.). The mixture was stirred and mixed. This was heated to 65° C. and stirred to dissolve. Furthermore, the resultant was placed in an oven at 80° C. and left to stand for 2 hours, and thus a homogeneous transparent oily matter was obtained. This was degassed under reduced pressure and was allowed to polymerize in an oven at 110° C. for one day and then at 130° C. for 3 hours.

The molded piece of the obtained resin had good transparency and had good external appearance without any distortion.

The refractive index of the obtained resin was measured, and the refractive index ne was 1.642 and the Abbe number ve was 37.

Example 4

1.0 g of the compound produced in the Reference Preparation Example 2 was weighed in a glass beaker, and 1.0 g of the compound produced in Example 1 was added thereto, under room temperature (25° C.). The mixture was stirred and mixed. This was heated to 75° C. and stirred to dissolve. Furthermore, the resultant was placed in an oven at 100° C. and left to stand for 1 hour, and thus a homogeneous transparent oily matter was obtained. This was degassed under reduced pressure and was allowed to polymerize in an oven at 110° C. for 3 days and then at 130° C. for 3 hours.

The molded piece of the obtained resin had good transparency and had good external appearance without any distortion.

The refractive index of the obtained resin was measured, and the refractive index ne was 1.658 and the Abbe number ve was 40. These values were compared with the values of Example 3, and an effect of enhancing the refractive index and Abbe number by increasing the proportion of the compound produced in Example 1, was shown.

Comparative Example 1

2.17 g of norbornene diisocyanate was added into a glass beaker, and 1 mg of dibutyltin dichloride as a commercially available product was added thereto, under room temperature (25° C.). The mixture was stirred and dissolved. 1.83 g of 4-mercaptomethyl-1,8-dimercapto-3,6-dithiaoctane was added to the mixture, and the resulting mixture was stirred until it became homogeneous. This was degassed under reduced pressure, and was allowed to polymerize in a polymerization oven over 21 hours while the temperature was slowly increased from 20° C. to 120° C.

The molded piece of the obtained resin had good transparency and had good external appearance without any distortion.

The refractive index of the obtained resin was measured, and the refractive index ne was 1.623 and the Abbe number ve was 38.

Example 5

0.25 g of the compound produced in the Reference Preparation Example 2 was weighed in a glass beaker, and 0.25 g of the compound produced in Example 1 was added thereto, under room temperature (25° C.). The mixture was stirred and mixed. This was heated to 75° C. and stirred to dissolve. Furthermore, the resultant was placed in an oven at 100° C. and left to stand for 1 hour, and thus a homogeneous transparent oily matter was obtained. 0.48 g of 4-mercaptomethyl-1,8-dimercapto-3,6-dithiaoctane was added to the mixture, and the resulting mixture was stirred until it became homogeneous. Subsequently, the mixture was cooled to room temperature, and 0.57 g of norbornene diisocyanate was added thereto and stirred. This was degassed under reduced pressure, and was allowed to polymerize in a polymerization oven over 21 hours while the temperature was slowly increased from 20° C. to 120° C.

The molded piece of the obtained resin had good transparency and had good external appearance without any distortion.

The refractive index of the obtained resin was measured, and the refractive index ne was 1.634 and the Abbe number ve was 39. These values were compared with the values of Comparative Example 1, and an effect of enhancing the refractive index and Abbe number by adding the compound produced in Reference Preparation Example 2, was shown.

Example 6

In the present Example, synthesis of neodymium(III) tris(thietanylthioacetate) (compound represented by the following formula (11)) was carried out.

A mixture obtained by adding 18.2 g of pure water to 18.2 g (0.11 moles) of thietanylthioacetic acid synthesized in the Reference Preparation Example 2, was heated to 35° C. using a warm water bath, and the mixture was stirred and dispersed to obtain a solution. 3.4 g of neodymium oxide (0.01 moles: commercially available product (manufactured by Wako Pure Chemical Industries, Ltd.)) was added into the solution, and the mixture was allowed to react for 24 hours under stirring. This solution was filtered to remove the insoluble matter, and the filtrate was poured into 200 g of ethanol and stirred to allow crystallization. The precipitated light purple solids were collected by filtration, washed with ethanol, and dried under reduced pressure. Thus, 8.1 g of the target product, neodymium(III) tris(thietanylthioacetate), was obtained. The yield was 86%.

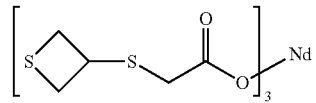

(11)

The identification data of the obtained compounds are shown below.

$^1$H-NMR (solvent: DMSO-d6, internal standard substance: TMS) δ: 3.36 (6H), 3.63 (6H), 4.63 (6H), 5.10 (3H). All broad absorptions.

IR (Universal ATR method): 1535, 1387, 1218, 1168, 1040, 949, 705, 574, 444 cm$^{-1}$.

Example 7

In the present Example, synthesis of gadolinium(III) tris(thietanylthioacetate) (compound represented by the following formula (12)) was carried out.

18.0 g of pure water was added to 18.0 g (0.11 moles) of thietanylthioacetic acid synthesized in the Reference Preparation Example 2, and then the mixture was heated to 35° C. in a warm water bath and was stirred and dispersed. To this solution, 3.6 g of gadolinium oxide (0.01 moles: commercially available product (manufactured by Wako Pure Chemical Industries, Ltd.)) was added, and the mixture was allowed to react for 2 days under stirring. This solution was filtered to remove the insoluble matter, and was poured into 150 g of ethanol to allow crystallization. The precipitated white solids were collected by filtration, washed with ethanol, and then dried under reduced pressure. Thus, 3.8 g of the target product, gadolinium(III) tris(thietanylthioacetate), was obtained. The yield was 29%.

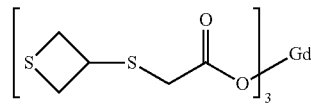

(12)

The identification data of the obtained compounds are shown below.

$^1$H-NMR (solvent: DMSO-d6, internal standard substance: TMS) Broad peaks were obtained, so that measurement was impossible.

IR (Universal ATR method): 1547, 1386, 1223, 1168, 1040, 950, 704, 651, 588, 446 cm$^{-1}$.

Example 8

In the present Example, synthesis of cerium(III) tris(thietanylthioacetate) (compound represented by the following formula (13)) was carried out.

20.0 g of pure water was added to 20.0 g (0.12 moles) of thietanylthioacetic acid synthesized in the Reference Preparation Example 2, and then the mixture was heated to 35° C. in a warm water bath and was stirred and dispersed. To this solution, 6.0 g of cerium carbonate (0.01 moles: commercially available product (manufactured by Wako Pure Chemical Industries, Ltd.)) was added, and the mixture was allowed to react for 2 days under stirring. This solution was filtered to remove the insoluble matter, and was poured into 150 g of ethanol to allow crystallization. The precipitated white solids were collected by filtration, washed with ethanol, and then dried under reduced pressure. Thus, 11.2 g of the target product, cerium(III) tris(thietanylthioacetate), was obtained. The yield was 89%.

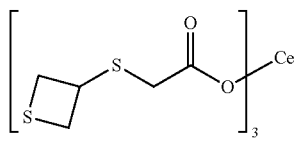

(13)

The identification data of the obtained compounds are shown below.

$^1$H-NMR (solvent: DMSO-d6, internal standard substance: TMS) δ: 3.26 (6H), 3.50 (6H), 4.03 (6H), 4.84 (3H). All broad absorptions.

$^{13}$C-NMR (solvent: DMSO-d6) δ: 34.1, 42.7, 44.5, 170.8.

IR (Universal ATR method): 1546, 1384, 1222, 1168, 1041, 949, 701, 579, 447 cm$^{-1}$.

(Preparation of Polymerizable Composition and Production of Cured Resin Product by Polymerization of the Composition)

In the following Examples, polymerizable compositions were prepared using the thietane compounds produced in the above Preparation Examples or Examples, and these compositions were cured by polymerization to obtain resins.

The properties of the obtained resins or optical components (lenses) were evaluated by the methods shown below.

External appearance: Transparency was checked by visual inspection.

Refractive index, Abbe number: Measured at 20° C. using a Pulfrich refractometer.

Example 9

1.8 g of the compound produced in the Reference Preparation Example 2 was weighed in a glass beaker, and 1.2 g of the compound produced in Example 6 was added thereto, under room temperature (25° C.). The mixture was stirred and mixed. This was heated to 70° C. and stirred to dissolve. Furthermore, the resulting homogeneous transparent oily matter was degassed under reduced pressure in an oven at 70° C., and then the oily matter was placed in an oven at 80° C. and left to stand for 14 hours. The temperature was increased up to 120° C. over 4 hours, and was allowed to polymerize for 3 days at 120° C.

The molded piece of the obtained resin had a purple color and good transparency and had good external appearance without any distortion.

The refractive index and Abbe number of the obtained resin were measured, and the refractive index ne was 1.649 and the Abbe number νe was 37.6.

Example 10

1.2 g of the compound produced in the Reference Preparation Example 2 was weighed in a glass beaker, and 1.8 g of the compound produced in Example 6 was added thereto, under room temperature (25° C.). The mixture was stirred and mixed. This was heated to 70° C. and stirred to dissolve. Furthermore, the resulting homogeneous transparent oily matter was degassed under reduced pressure in an oven at 70° C., and then the oily matter was placed in an oven at 80° C. and left to stand for 14 hours. The temperature was increased up to 120° C. over 4 hours, and was allowed to polymerize for 3 days at 120° C.

The molded piece of the obtained resin had a purple color and good transparency and had good external appearance without any distortion.

The refractive index and Abbe number of the obtained resin were measured, and the refractive index ne was 1.653 and the Abbe number νe was 38.4. When this Example is compared with Example 4, a tendency was observed that both the refractive index and Abbe number increase when the proportion of the compound produced in Example 1 is increased.

Example 11

1.0 g of the compound produced in the Reference Preparation Example 2 was weighed in a glass beaker at room temperature (25° C.), and 1.0 g of the compound produced in Example 7 was added thereto. The mixture was stirred and mixed. This was heated to 70° C. and stirred to dissolve. Furthermore, the resulting homogeneous transparent oily matter was degassed under reduced pressure in an oven at 70° C., and then the oily matter was placed in an oven at 80° C. and left to stand for 14 hours. The temperature was increased up to 120° C. over 4 hours, and was allowed to polymerize for 3 days at 120° C.

The molded piece of the obtained resin was colorless, had good transparency, and had good external appearance without any distortion.

The refractive index and Abbe number of the obtained resin were measured, and the refractive index ne was 1.665 and the Abbe number νe was 39.6.

Example 12

0.4 g of the compound produced in the Reference Preparation Example 2 was weighed in a glass beaker at room temperature (25° C.), and 1.6 g of the compound produced in Example 8 was added thereto. The mixture was stirred and mixed. This was heated to 70° C. and stirred to dissolve. Furthermore, the resulting homogeneous transparent oily matter was degassed under reduced pressure in an oven at 70° C., and then the oily matter was placed in an oven at 80° C. and left to stand for 14 hours. The temperature was increased up to 120° C. over 4 hours, and was allowed to polymerize for 3 days at 120° C.

The molded piece of the obtained resin was colorless, had good transparency, and had good external appearance without any distortion.

The refractive index and Abbe number of the obtained resin were measured, and the refractive index ne was 1.663 and the Abbe number νe was 38.3.

Reference Preparation Example 3

Ethanedithiol (99.7 g) and water (150 g) were added into a reactor equipped with a stirrer and a thermometer. A 31% aqueous solution of sodium hydroxide (55.6 g) was added dropwise thereto, and then stirring was continued for one hour at room temperature. This mixture was cooled to 5° C., and then an aqueous solution prepared by dissolving monochloroacetic acid (20.0 g) in water (150 g) was added dropwise over 30 minutes. The mixture was returned to room temperature, and stirring was continued for 5 hours. Toluene (40 g) was added to the obtained reaction mixture, and an operation of removing excess ethanedithiol through extraction and partition into the toluene layer was repeated two times. 35% hydrochloric acid was added to the aqueous layer to adjust the pH to 1, and then an extraction operation was performed two times with ethyl acetate (200 g). The obtained ethyl acetate layer was dried over magnesium sulfate, and then was filtered to remove salts. The filtrate was concentrated under reduced pressure, and thereby the solvent was distilled off. The obtained oil was purified by silica gel chromatography (silica gel 500 g, dichloromethane/acetone=7/1+ acetic acid 0.2 vol %), and thus a colorless liquid (11.0 g) was obtained. As a result of an analysis, the product was found to be 2-mercaptoethylthioacetic acid. The identification data and structural formula (formula (108)) thus obtained are shown below.

$^1$H-NMR (solvent: DMSO-d6, internal standard substance: TMS) δ: 2.51 (1H), 2.68 (2H), 2.79 (2H), 3.28 (2H), 12.57 (1H)

IR (Universal ATR method): 2917, 2672, 2555, 1699, 1420, 1291, 1197, 1128, 893, 783, 694, 577, 460 cm$^{-1}$ FAB (Neg)-MS (matrix: m-nitrobenzyl alcohol): m/z 151 (M-H)$^-$

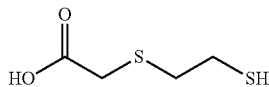

(108)

Example 13

The compound of Reference Preparation Example 3 (6.48 g), water (150 g) and DMF (150 g) were added into a reactor equipped with a stirrer and a thermometer, and while stirring the mixture, lanthanum carbonate (2.5 g) was added thereto. Subsequently, the mixture was heated to 60° C., and stirring was continued for 10 hours. Solids were removed by filtration, and then the filtrate was concentrated under reduced pressure. When acetone (250 g) was added to the obtained concentrate, and the mixture was stirred, a colorless oily matter was generated. The acetone layer was removed by decantation, and the resulting oily matter was dried under reduced pressure, to obtain a white solid (4.2 g). As a result of an analysis, the product was found to be lanthanum(III) 2-mercaptoethylthioacetate. The identification data and structural formula (formula (106)) thus obtained are shown below.

$^1$H-NMR (solvent: DMSO-d6, internal standard substance: TMS) δ: 2.50 (3H), 2.70 (6H), 2.78 (6H), 3.07 (6H)

IR (Universal ATR method): 2539, 1538, 1382, 1208, 1150, 943, 789, 693, 582, 446 cm$^{-1}$ FAB(Neg)-MS (matrix: DMDS, glycerin): m/z 591 (M-H)$^-$

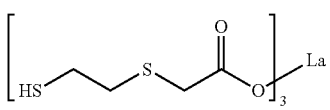

(106)

Example 14

N-acetylcysteine (8.45 g) and water (200 g) were added into a reactor equipped with a stirrer and a thermometer, and while stirring the mixture, lanthanum carbonate (4.0 g) was added thereto. Subsequently, the mixture was heated to 40° C., and stirring was continued for 10 hours. Solids were removed by filtration, and then the filtrate was concentrated under reduced pressure to distill off the solvent. Acetone (200 g) was added to the concentrate, and the mixture was stirred. Generated precipitates were obtained as a white solid (9.8 g) by filtration and were dried under reduced pressure. As a result of an analysis, the product was found to be a lanthanum complex of N-acetylcysteine. The identification data and structural formula (formula (107)) thus obtained are shown below.

$^1$H-NMR (solvent: DMSO-d6, internal standard substance: TMS) δ: 1.89 (9H), 2.23 (3H), 2.80 (6H), 3.40 (3H), 4.24 (3H), 7.72 (3H)

IR (Universal ATR method): 2548, 1557, 1404, 1292, 1126, 1039, 980, 675, 592, 539 cm$^{-1}$ FAB(Neg)-MS (matrix: DMDS, glycerin): m/z 624 (M-H)$^-$

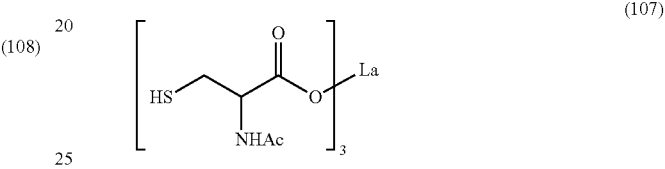

(107)

Example 15

The compound of Example 13 (2.0 wt %) was dissolved in a mixture of 2-mercaptoethanol (7.9 wt %) and 4-mercaptomethyl-3,6-dithiaoctane-1,8-dithiol (31.7 wt %), and then the mixture was degassed under reduced pressure. To this, norbornene diisocyanate (58.4 wt %) which had been degassed under reduced pressure in advance, was added, and the mixture was mixed under cooling at 5° C., to obtain a homogeneous solution. This mixed solution was polymerized by slowly heating over 20 hours from 25° C. to 120° C., and thus a transparent resin was obtained.

The property values of the transparent resin thus obtained are presented in Table 1.

Examples 16 and 17

The same operation was carried out, except that the composition of the respective monomers in Example 15 was changed to the compositions shown in Table 1. The property values of the transparent resin thus obtained are presented in Table 1.

Reference Example 1

A mixture of 2-mercaptoethanol (8.2 wt %) and 4-mercaptomethyl-3,6-dithiaoctane-1,8-dithiol (32.7 wt %) was degassed under reduced pressure. A solution obtained by dissolving dibutyltin dichloride (0.15 wt %) as a catalyst in norbornene diisocyanate (59.1 wt %) and degassing the mixture under reduced pressure, was added to the previous thiol mixture, and thus a homogeneous solution was obtained. This mixed solution was polymerized by slowly heating over 20 hours from 25° C. to 120° C., and thus a transparent resin was obtained.

The property values of the transparent resin thus obtained are presented in Table 1.

TABLE 1

| | Composition (wt %) | | | | | Resin properties | |
|---|---|---|---|---|---|---|---|
| | Thiol A | Thiol B | La complex A | Isocyanate A | Catalyst A | Refractive index (ne) | Abbe number (ve) |
| Example 15 | 31.7 | 7.9 | 2.0 | 58.4 | — | 1.606 | 40.0 |
| Example 16 | 30.6 | 7.6 | 4.2 | 57.6 | — | 1.606 | 39.7 |
| Example 17 | 29.4 | 7.4 | 6.5 | 56.7 | — | 1.607 | 39.8 |
| Ref. Ex. 1 | 32.7 | 8.2 | 0.0 | 59.1 | 1500 ppm | 1.605 | 40.0 |

Thiol A: 4-Mercaptomethyl-3,6-dithiaoctane-1,8-dithiol
Thiol B: 2-Mercaptoethanol
La Complex A: Compound of Example 3
Isocyanate A: Xylene diisocyanate
Catalyst A: Dibutyltin dichloride Example 18

The compound of Example 13 (2.2 wt %) was dissolved in a mixture of 2-mercaptoethanol (6.4 wt %) and 4-mercaptomethyl-3,6-dithiaoctane-1,8-dithiol (36.5 wt %), and then the mixture was degassed under reduced pressure. To this, xylene diisocyanate (54.9 wt %) which had been degassed under reduced pressure in advance, was added, and the mixture was mixed under cooling at 5° C., to obtain a homogeneous solution. This mixture was polymerized by slowly heating over 20 hours from 25° C. to 120° C., and thus a transparent resin was obtained.

The property values of the transparent resin thus obtained are presented in Table 2.

Reference Example 2

A mixture of 2-mercaptoethanol (6.7 wt %) and 4-mercaptomethyl-3,6-dithiaoctane-1,8-dithiol (37.7 wt %) was degassed under reduced pressure. A solution obtained by dissolving dibutyltin dichloride (0.035 wt %) as a catalyst in norbornene diisocyanate (55.6 wt %) and degassing the mixture under reduced pressure, was added to the previous thiol mixture, and thus a homogeneous solution was obtained. This mixture was polymerized by slowly heating over 20 hours from 25° C. to 120° C., and thus a transparent resin was obtained.

The property values of the transparent resin thus obtained are presented in Table 2.

The invention claimed is:

1. A metal compound represented by the following formula (1):

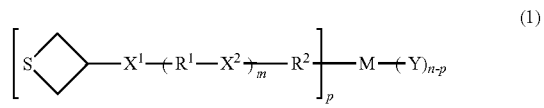

wherein $X^1$ and $X^2$ each independently represent a sulfur atom or an oxygen atom; $R^1$ represents a divalent organic group; $R^2$ represents a $CH_2(C=O)O-$ group; m represents an integer of 0 or not less than 1; M represents a lanthanoid atom or a Ba atom; n represents the valence of M; p represents an integer of 1 to n;

Y represents a monovalent inorganic or organic group; when n–p is not less than 2, a plurality of Y's each independently represent a monovalent inorganic or organic group; and when n–p is not less than 2, the plurality of Y's may be bonded with each other to form a ring containing M.

2. The metal compound as set forth in claim 1, wherein M is a lanthanum (La) atom.

3. The metal compound as set forth in claim 1, wherein M is any one of a neodymium (Nd) atom, a gadolinium (Gd) atom and a cerium (Ce) atom.

4. The metal compound as set forth in claim 2, wherein m=0.

TABLE 2

| | Composition (wt %) | | | | | Resin properties | |
|---|---|---|---|---|---|---|---|
| | Thiol A | Thiol B | La complex A | Isocyanate B | Catalyst A | Refractive index (ne) | Abbe number (ve) |
| Example 18 | 36.5 | 6.4 | 2.2 | 54.9 | — | 1.653 | 31.7 |
| Ref. Ex. 2 | 37.7 | 6.7 | 0.0 | 55.6 | 350 ppm | 1.653 | 31.9 |

Thiol A: 4-Mercaptomethyl-3,6-dithiaoctane-1,8-dithiol
Thiol B: 2-Mercaptoethanol
La Complex A: Compound of Example 3
Isocyanate B: Norbornene diisocyanate
Catalyst A: Dibutyltin dichloride 5. The metal compound as set forth in claim 4, wherein $X^1$ represents a sulfur atom.

6. The metal compound as set forth in claim 1, wherein n=p.

7. A polymerizable composition containing the metal compound as set forth in claim 1.

8. The polymerizable composition as set forth in claim 7, comprising said metal compound, and
further comprising one or more kind selected from the group consisting of an isocyanate compound, an active hydrogen compound, an epoxy compound, an epithio compound, and a thietane compound.

9. The polymerizable composition as set forth in claim 7, further comprising a bluing agent.

10. A method for producing a resin, the method comprising cast polymerizing the polymerizable composition as set forth in claim 7.

11. A resin obtainable by polymerizing the polymerizable composition as set forth in claim 7.

12. An optical component formed from the resin as set forth in claim 11.

* * * * *